(12) United States Patent
Wood et al.

(10) Patent No.: US 11,858,982 B2
(45) Date of Patent: Jan. 2, 2024

(54) CANCER TREATMENT WITH AN ANTIBODY

(71) Applicant: MedAnnex Ltd., Edinburgh (GB)

(72) Inventors: Christopher Barry Wood, Edinburgh (GB); Tina C. Flatau, Edinburgh (GB); Fiona Dempsey, Edinburgh (GB); Scott Crichton, Edinburgh (GB)

(73) Assignee: MEDANNEX LTD., Edinburgh (GB)

( * ) Notice: Subject to any disclaimer, the term of this patent is extended or adjusted under 35 U.S.C. 154(b) by 375 days.

(21) Appl. No.: 17/266,883

(22) PCT Filed: Aug. 12, 2019

(86) PCT No.: PCT/EP2019/071627
§ 371 (c)(1),
(2) Date: Feb. 8, 2021

(87) PCT Pub. No.: WO2020/030827
PCT Pub. Date: Feb. 13, 2020

(65) Prior Publication Data
US 2021/0238269 A1  Aug. 5, 2021

(30) Foreign Application Priority Data
Aug. 10, 2018 (GB) ...................................... 1813137

(51) Int. Cl.
| | |
|---|---|
| *C07K 16/18* | (2006.01) |
| *A61P 35/00* | (2006.01) |
| *A61K 39/395* | (2006.01) |
| *A61K 45/06* | (2006.01) |
| *C07K 16/30* | (2006.01) |
| *A61K 39/00* | (2006.01) |

(52) U.S. Cl.
CPC ........ *C07K 16/18* (2013.01); *A61K 39/39558* (2013.01); *A61K 45/06* (2013.01); *A61P 35/00* (2018.01); *C07K 16/30* (2013.01); *A61K 2039/505* (2013.01); *C07K 2317/24* (2013.01); *C07K 2317/34* (2013.01); *C07K 2317/73* (2013.01)

(58) Field of Classification Search
CPC .. C07K 16/18; C07K 16/30; A61K 39/39558; A61K 45/06
See application file for complete search history.

(56) References Cited

U.S. PATENT DOCUMENTS

| | | | |
|---|---|---|---|
| 9,127,051 B2 * | 9/2015 | D'Acquisto | ............ A61P 17/00 |
| 11,041,019 B2 * | 6/2021 | Hays | ..................... A61K 51/087 |
| 2015/0086553 A1 | 3/2015 | Han et al. | |
| 2020/0031911 A1 * | 1/2020 | Hays | ........................ A61P 25/18 |
| 2020/0171165 A1 | 6/2020 | Schnitzer et al. | |
| 2021/0292400 A1 | 9/2021 | Han et al. | |

FOREIGN PATENT DOCUMENTS

| | | |
|---|---|---|
| EP | 2 551 347 | 1/2013 |
| WO | 99/21980 | 5/1999 |
| WO | 2004/055519 | 7/2004 |
| WO | 2005/027965 | 3/2005 |
| WO | 2005/117848 | 12/2005 |
| WO | 2010/064012 | 6/2010 |
| WO | 2011/154705 | 12/2011 |
| WO | 2013/088111 | 6/2013 |
| WO | 2015/039175 | 3/2015 |
| WO | 2018/146230 | 8/2018 |
| WO | 2019/222618 | 11/2019 |
| WO | 2020/033467 | 2/2020 |

OTHER PUBLICATIONS

Almagro & Fransson, Humanization of antibodies, Frontiers in Bioscience 2008; 13: 1619-33 (Year: 2008).*
Riemer et al., Matching of trastuzumab (Herceptin®) epitope mimics onto the surface of Her-2/neu—a new method of epitope definition, Mol Immunol, 2005 42(9): 1121-1124 (Year: 2005).*
Rudikoff et al., Single amino acid substitution altering antigen-binding specificity, PNAS, USA, 1982, 79: 1979-1983 (Year: 1982).*
Gura, T., Systems for Identifying New Drugs Are Often Faulty, Science, 1997, 278:1041-1042 (Year: 1997).*
Kaiser, J., First pass at cancer genoome reveals complex landscape, Science, 2006, 313:1370 (Year: 2006).*
Chames et al., Therapeutic antibodies: successes, limitations and hopes for the future, British J. of Pharmacology, 2009, 157, 220-233 (Year: 2009).*
Tannock, 19 Experimental Chemotherapy, The Basic Science of Oncology, 2nd Edition, Publish Year: 1992 (Year: 1992).*
International Search Report and Written Opinion of the International Searching Authority, dated Oct. 31, 2019 in corresponding International Patent Application No. PCT/EP2019/071627.
Pan et al., "Downregulation of Annexin A1 by short hairpin RNA inhibits the osteogenic differentiation of rat bone marrow-derived mesenchymal stem cells", International Journal of Molecular Medicine, 36(2): 406-414 (2015).
Moraes et al., "Annexin-A1 enhances breast cancer growth and migration by promoting alternative macrophage polarization in the tumour microenVironment", Scientific Reports, 7:17925, 12 pages (2017), XPSS633676.
Mussunoor et al., "The role of annexins in tumour development and progression", Journal of Pathology, 216(2): 131-140 (2008).
Boudhraa et al., "Annexin A1 localization and its relevance to cancer", Clinical Science, 130(4): 205-220 (2016).
D'Acquisto, F. et al., "Annexin-1 modulates T-cell activation and differentiation", Blood, vol. 109, No. 3, 2007, pp. 1095-1102.
D'Acquisto, F. et al., "Annexin-A1: a pivotal regulator of the innate and adaptive immune systems", British Journal of Pharmacology, vol. 155, 2008, pp. 152-169.

(Continued)

*Primary Examiner* — Peter J Reddig
*Assistant Examiner* — Cheng Lu
(74) *Attorney, Agent, or Firm* — WENDEROTH, LIND & PONACK, L.L.P.

(57) ABSTRACT

The present invention provides antibodies that bind human Anx-A1 for use in the treatment of cancer, including drug-resistant cancer. Kits and products for this use are also provided.

17 Claims, 11 Drawing Sheets

Specification includes a Sequence Listing.

(56) References Cited

OTHER PUBLICATIONS

Frenzel, A. et al., "Designing Human Antibodies by Phage Display", Transfusion Medicine and Hemotherapy, vol. 44, No. 5, 2017, pp. 312-318.

Housman, G. et al., "Drug Resistance in Cancer: An Overview", Cancers, vol. 6, 2014, pp. 1769-1792.

Oh, P. et al., "Subtractive proteomic mapping of the endothelial surface in lung and solid tumours for tissue-specific therapy", Nature, vol. 429, 2004, pp. 629-635.

Shen, D-W. et al., "Cisplatin Resistance: A Cellular Self-Defense Mechanism Resulting from Multiple Epigenetic and Genetic Changes", Pharmacological Reviews, vol. 64, 2012, pp. 706-721.

Rodrigo, G. et al, Antibody Fragments and Their Purification by Protein L Affinity Chromatography, Antibodies, vol. 4, No. 3, 2015, pp. 259-277.

Volm, M. et al., "Prediction of Cancer Drug Resistance and Implications for Personalized Medicine", Frontiers in Oncology, vol. 5, Article 282, 2015, 14 pages.

Wang, Y. et al., "Annexin-I expression modulates drug resistance in tumor cells", Biochemical and Biophysical Research Communications, vol. 314, 2004, pp. 565-570.

Wang, J. et al., "Insider information: Testing cancer drug sensitivity for personalized therapy", Genes and Diseases, vol. 2, 2015, pp. 219-221.

Barderas, R. et al., "Affinity maturation of antibodies assisted by in silico modeling", PNAS, vol. 105, No. 26, 2008, pp. 9029-9034.

Brown, M. et al., "Tolerance of single, but not multiple, amino acid replacements in antibody VH CDR 2: a means of minimizing B cell wastage from somatic hypermutation?", Journal of Immunology, vol. 156, 1996, pp. 3285-3291.

Cai, X. et al., "Preparation and identification of monoclonal antibody against annexin I", Tumor, vol. 26, 2006, pp. 979-983, with English abstract thereof.

D'Angelo, S. et al., "Many Routes to an Antibody Heavy-Chain CDR3: Necessary, Yet Insufficient, for Specific Binding", Frontiers in Immunology, vol. 9, Article 395, 2018, 13 pages.

Falini, B. et al., Simple diagnostic assay for hairy cell leukaemia by immunocytochemical detection of annexin A1 (ANXA1), The Lancet, vol. 363, 2004, pp. 1869-1871.

Flower, R.J. et al., "Lipocortin-1: cellular mechanisms and clinical relevance", Trends in Pharmacological Sciences, vol. 15, 1994, pp. 71-76.

Maynard, J.A. et al., "Protection against anthrax toxin by recombinant antibody fragments correlates with antigen affinity", Nature Biotechnology, vol. 20, 2002, pp. 597-601.

Rudikoff, S. et al., "Single amino acid substitution altering antigen-binding specificity", PNAS, vol. 79, 1982, pp. 1979-1983.

Tu, Y. et al., "Annexin A1 influences in breast cancer: Controversies on contributions to tumour, host and immunoediting processes", Pharmacological Research, vol. 119, 2017, pp. 278-288.

Vajdos, F.F. et al., "Comprehensive Functional Maps of the Antigen-binding Site of an Anti-ErbB2 Antibody Obtained with Shotgun Scanning Mutagenesis", Journal of Molecular Biology, vol. 320, 2002, pp. 415-428.

Weyd, H. et al., "Annexin A1 on the Surface of Early Apoptotic Cells Suppresses $CD8^+$ T Cell Immunity", PLoS One, vol. 8, Issue No. 4, Apr. 2013, 13 pages.

Winkler, K. et al, "Changing the Antigen Binding Specificity by Single Point Mutations of an Anti-p24 (HIV-11 Antibody)", Journal of Immunology, vol. 165, 2000, pp. 4505-4514.

Xu, J.L. et al., "Diversity in the CDR34 Region of $V_H$ is Sufficient for Most Antibody Specificities", Immunity, vol. 13, 2000, pp. 37-45.

Zhang, G. et al., "Cisplatin treatment leads to changes in nuclear protein and microRNA expression", Mutation Research, 2012, vol. 746, pp. 66-77.

* cited by examiner

```
                        SEQUENCE LISTING

<160> NUMBER OF SEQ ID NOS: 31

<210> SEQ ID NO 1
    <211> LENGTH: 16
    <212> TYPE: PRT
    <213> ORGANISM: Artificial Sequence
    <220> FEATURE:
    <223> OTHER INFORMATION: VLCDR1 of L1M2H4 and L2M2H2

<400> SEQUENCE: 1

Arg Ser Ser Gln Ser Leu Glu Asn Ser Asn Ala Lys Thr Tyr Leu Asn
    1               5                   10                  15

<210> SEQ ID NO 2
    <211> LENGTH: 7
    <212> TYPE: PRT
    <213> ORGANISM: Artificial Sequence
    <220> FEATURE:
    <223> OTHER INFORMATION: VLCDR2 of Mdx001, L1M2H4 and L2M2H2

<400> SEQUENCE: 2

Gly Val Ser Asn Arg Phe Ser
    1               5

<210> SEQ ID NO 3
    <211> LENGTH: 9
    <212> TYPE: PRT
    <213> ORGANISM: Artificial Sequence
    <220> FEATURE:
    <223> OTHER INFORMATION: VLCDR3 of Mdx001, L1M2H4 and L2M2H2

<400> SEQUENCE: 3

Leu Gln Val Thr His Val Pro Tyr Thr
    1               5

<210> SEQ ID NO 4
    <211> LENGTH: 10
    <212> TYPE: PRT
    <213> ORGANISM: Artificial Sequence
    <220> FEATURE:
    <223> OTHER INFORMATION: VHCDR1 of Mdx001, L1M2H4 and L2M2H2

<400> SEQUENCE: 4

Gly Tyr Thr Phe Thr Asn Tyr Trp Ile Gly
    1               5                   10

<210> SEQ ID NO 5
    <211> LENGTH: 17
```

```
-continued

<212> TYPE: PRT
<213> ORGANISM: Artificial Sequence
<220> FEATURE:
<223> OTHER INFORMATION: VHCDR2 of Mdx001, L1M2H4 and L2M2H2

<400> SEQUENCE: 5

Asp Ile Tyr Pro Gly Gly Asp Tyr Thr Asn Tyr Asn Glu Lys Phe Lys
1               5                   10                  15

Gly

<210> SEQ ID NO 6
<211> LENGTH: 11
<212> TYPE: PRT
<213> ORGANISM: Artificial Sequence
<220> FEATURE:
<223> OTHER INFORMATION: VHCDR3 of Mdx001, L1M2H4 and L2M2H2

<400> SEQUENCE: 6

Ala Arg Trp Gly Leu Gly Tyr Tyr Phe Asp Tyr
1               5                   10

<210> SEQ ID NO 7
<211> LENGTH: 16
<212> TYPE: PRT
<213> ORGANISM: Artificial Sequence
<220> FEATURE:
<223> OTHER INFORMATION: VLCDR1 of Mdx001

<400> SEQUENCE: 7

Arg Ser Ser Gln Ser Leu Glu Asn Ser Asn Gly Lys Thr Tyr Leu Asn
1               5                   10                  15

<210> SEQ ID NO 8
<211> LENGTH: 16
<212> TYPE: PRT
<213> ORGANISM: Artificial Sequence
<220> FEATURE:
<223> OTHER INFORMATION: VLCDR1 variant with S9T substitution

<400> SEQUENCE: 8

Arg Ser Ser Gln Ser Leu Glu Asn Thr Asn Gly Lys Thr Tyr Leu Asn
1               5                   10                  15

<210> SEQ ID NO 9
<211> LENGTH: 112
<212> TYPE: PRT
<213> ORGANISM: Artificial Sequence
<220> FEATURE:
<223> OTHER INFORMATION: L1M2 light chain variable region

<400> SEQUENCE: 9

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Glu Asn Ser
            20                  25                  30

Asn Ala Lys Thr Tyr Leu Asn Trp Phe Gln Gln Arg Pro Gly Gln Ser
        35                  40                  45

Pro Arg Arg Leu Ile Tyr Gly Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Leu Gln Val
                85                  90                  95
```

```
Thr His Val Pro Tyr Thr Phe Gly Gln Gly Thr Lys Leu Glu Ile Lys
            100                 105                 110
```

<210> SEQ ID NO 10
<211> LENGTH: 112
<212> TYPE: PRT
<213> ORGANISM: Artificial Sequence
<220> FEATURE:
<223> OTHER INFORMATION: L2M2 light chain variable region

<400> SEQUENCE: 10

```
Asp Ile Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Glu Asn Ser
            20                  25                  30

Asn Ala Lys Thr Tyr Leu Asn Trp Tyr Leu Gln Lys Pro Gly Gln Ser
        35                  40                  45

Pro Gln Leu Leu Ile Tyr Gly Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Leu Gln Val
                85                  90                  95

Thr His Val Pro Tyr Thr Phe Gly Gln Gly Thr Lys Val Glu Ile Lys
            100                 105                 110
```

<210> SEQ ID NO 11
<211> LENGTH: 118
<212> TYPE: PRT
<213> ORGANISM: Artificial Sequence
<220> FEATURE:
<223> OTHER INFORMATION: H4 heavy chain variable region

<400> SEQUENCE: 11

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asn Tyr
            20                  25                  30

Trp Ile Gly Trp Val Arg Gln Ala Pro Gly Gln Gly Leu Glu Trp Val
        35                  40                  45

Gly Asp Ile Tyr Pro Gly Gly Asp Tyr Thr Asn Tyr Asn Glu Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Gly Leu Gly Tyr Tyr Phe Asp Tyr Trp Gly Gln Gly Thr
            100                 105                 110

Met Val Thr Val Ser Ser
        115
```

<210> SEQ ID NO 12
<211> LENGTH: 118
<212> TYPE: PRT
<213> ORGANISM: Artificial Sequence
<220> FEATURE:
<223> OTHER INFORMATION: H2 heavy chain variable region

<400> SEQUENCE: 12

```
Gln Val Gln Leu Val Gln Ser Gly Pro Glu Val Lys Lys Pro Gly Glu
```

```
1               5                   10                  15
Ser Leu Lys Ile Ser Cys Lys Gly Ser Gly Tyr Thr Phe Thr Asn Tyr
                20                  25                  30

Trp Ile Gly Trp Val Arg Gln Ala Pro Gly Lys Gly Leu Glu Trp Met
        35                  40                  45

Gly Asp Ile Tyr Pro Gly Asp Tyr Thr Asn Tyr Asn Glu Lys Phe
    50                  55                  60

Lys Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Ile Tyr Tyr Cys
                85                  90                  95

Ala Arg Trp Gly Leu Gly Tyr Tyr Phe Asp Tyr Trp Gly Arg Gly Thr
            100                 105                 110

Leu Val Thr Val Ser Ser
            115
```

<210> SEQ ID NO 13
<211> LENGTH: 219
<212> TYPE: PRT
<213> ORGANISM: Artificial Sequence
<220> FEATURE:
<223> OTHER INFORMATION: L1M2 light chain

<400> SEQUENCE: 13

```
Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Glu Asn Ser
                20                  25                  30

Asn Ala Lys Thr Tyr Leu Asn Trp Phe Gln Gln Arg Pro Gly Gln Ser
            35                  40                  45

Pro Arg Arg Leu Ile Tyr Gly Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Leu Gln Val
                85                  90                  95

Thr His Val Pro Tyr Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 14
<211> LENGTH: 448
<212> TYPE: PRT

<213> ORGANISM: Artificial Sequence
<220> FEATURE:
<223> OTHER INFORMATION: H4 heavy chain

<400> SEQUENCE: 14

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asn Tyr
            20                  25                  30

Trp Ile Gly Trp Val Arg Gln Ala Pro Gly Gln Gly Leu Glu Trp Val
        35                  40                  45

Gly Asp Ile Tyr Pro Gly Gly Asp Tyr Thr Asn Tyr Asn Glu Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Gly Leu Gly Tyr Tyr Phe Asp Tyr Trp Gly Gln Gly Thr
            100                 105                 110

Met Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
```

```
                385                 390                 395                 400
Ser Asp Gly Ser Phe Phe Leu Tyr Ser Lys Leu Thr Val Asp Lys Ser
                    405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Lys
                435                 440                 445

<210> SEQ ID NO 15
<211> LENGTH: 219
<212> TYPE: PRT
<213> ORGANISM: Artificial Sequence
<220> FEATURE:
<223> OTHER INFORMATION: L2M2 light chain

<400> SEQUENCE: 15

Asp Ile Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Glu Asn Ser
            20                  25                  30

Asn Ala Lys Thr Tyr Leu Asn Trp Tyr Leu Gln Lys Pro Gly Gln Ser
        35                  40                  45

Pro Gln Leu Leu Ile Tyr Gly Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Leu Gln Val
                85                  90                  95

Thr His Val Pro Tyr Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 16
<211> LENGTH: 448
<212> TYPE: PRT
<213> ORGANISM: Artificial Sequence
<220> FEATURE:
<223> OTHER INFORMATION: H2 heavy chain

<400> SEQUENCE: 16

Gln Val Gln Leu Val Gln Ser Gly Pro Glu Val Lys Lys Pro Gly Glu
1               5                   10                  15

Ser Leu Lys Ile Ser Cys Lys Gly Ser Gly Tyr Thr Phe Thr Asn Tyr
            20                  25                  30
```

-continued

```
Trp Ile Gly Trp Val Arg Gln Ala Pro Gly Lys Gly Leu Glu Trp Met
         35                  40                  45
Gly Asp Ile Tyr Pro Gly Asp Tyr Thr Asn Tyr Asn Glu Lys Phe
 50                  55                  60
Lys Gly Gln Val Thr Ile Ser Ala Asp Lys Ser Ile Ser Thr Ala Tyr
 65                  70                  75                  80
Leu Gln Trp Ser Ser Leu Lys Ala Ser Asp Thr Ala Ile Tyr Tyr Cys
                 85                  90                  95
Ala Arg Trp Gly Leu Gly Tyr Tyr Phe Asp Tyr Trp Gly Arg Gly Thr
            100                 105                 110
Leu Val Thr Val Ser Ser Ala Ser Thr Lys Gly Pro Ser Val Phe Pro
        115                 120                 125
Leu Ala Pro Ser Ser Lys Ser Thr Ser Gly Gly Thr Ala Ala Leu Gly
    130                 135                 140
Cys Leu Val Lys Asp Tyr Phe Pro Glu Pro Val Thr Val Ser Trp Asn
145                 150                 155                 160
Ser Gly Ala Leu Thr Ser Gly Val His Thr Phe Pro Ala Val Leu Gln
                165                 170                 175
Ser Ser Gly Leu Tyr Ser Leu Ser Ser Val Val Thr Val Pro Ser Ser
            180                 185                 190
Ser Leu Gly Thr Gln Thr Tyr Ile Cys Asn Val Asn His Lys Pro Ser
        195                 200                 205
Asn Thr Lys Val Asp Lys Lys Val Glu Pro Lys Ser Cys Asp Lys Thr
    210                 215                 220
His Thr Cys Pro Pro Cys Pro Ala Pro Glu Leu Leu Gly Gly Pro Ser
225                 230                 235                 240
Val Phe Leu Phe Pro Pro Lys Pro Lys Asp Thr Leu Met Ile Ser Arg
                245                 250                 255
Thr Pro Glu Val Thr Cys Val Val Val Asp Val Ser His Glu Asp Pro
            260                 265                 270
Glu Val Lys Phe Asn Trp Tyr Val Asp Gly Val Glu Val His Asn Ala
        275                 280                 285
Lys Thr Lys Pro Arg Glu Glu Gln Tyr Asn Ser Thr Tyr Arg Val Val
    290                 295                 300
Ser Val Leu Thr Val Leu His Gln Asp Trp Leu Asn Gly Lys Glu Tyr
305                 310                 315                 320
Lys Cys Lys Val Ser Asn Lys Ala Leu Pro Ala Pro Ile Glu Lys Thr
                325                 330                 335
Ile Ser Lys Ala Lys Gly Gln Pro Arg Glu Pro Gln Val Tyr Thr Leu
            340                 345                 350
Pro Pro Ser Arg Asp Glu Leu Thr Lys Asn Gln Val Ser Leu Thr Cys
        355                 360                 365
Leu Val Lys Gly Phe Tyr Pro Ser Asp Ile Ala Val Glu Trp Glu Ser
    370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Lys Leu Thr Val Asp Lys Ser
                405                 410                 415
Arg Trp Gln Gln Gly Asn Val Phe Ser Cys Ser Val Met His Glu Ala
            420                 425                 430
Leu His Asn His Tyr Thr Gln Lys Ser Leu Ser Leu Ser Pro Gly Lys
        435                 440                 445
```

<210> SEQ ID NO 17
<211> LENGTH: 346
<212> TYPE: PRT
<213> ORGANISM: Homo sapiens

<400> SEQUENCE: 17

Met Ala Met Val Ser Glu Phe Leu Lys Gln Ala Trp Phe Ile Glu Asn
1               5                   10                  15

Glu Glu Gln Glu Tyr Val Gln Thr Val Lys Ser Ser Lys Gly Gly Pro
            20                  25                  30

Gly Ser Ala Val Ser Pro Tyr Pro Thr Phe Asn Pro Ser Ser Asp Val
        35                  40                  45

Ala Ala Leu His Lys Ala Ile Met Val Lys Gly Val Asp Glu Ala Thr
    50                  55                  60

Ile Ile Asp Ile Leu Thr Lys Arg Asn Asn Ala Gln Arg Gln Gln Ile
65                  70                  75                  80

Lys Ala Ala Tyr Leu Gln Glu Thr Gly Lys Pro Leu Asp Glu Thr Leu
                85                  90                  95

Lys Lys Ala Leu Thr Gly His Leu Glu Glu Val Val Leu Ala Leu Leu
            100                 105                 110

Lys Thr Pro Ala Gln Phe Asp Ala Asp Glu Leu Arg Ala Ala Met Lys
        115                 120                 125

Gly Leu Gly Thr Asp Glu Asp Thr Leu Ile Glu Ile Leu Ala Ser Arg
    130                 135                 140

Thr Asn Lys Glu Ile Arg Asp Ile Asn Arg Val Tyr Arg Glu Glu Leu
145                 150                 155                 160

Lys Arg Asp Leu Ala Lys Asp Ile Thr Ser Asp Thr Ser Gly Asp Phe
                165                 170                 175

Arg Asn Ala Leu Leu Ser Leu Ala Lys Gly Asp Arg Ser Glu Asp Phe
            180                 185                 190

Gly Val Asn Glu Asp Leu Ala Asp Ser Asp Ala Arg Ala Leu Tyr Glu
        195                 200                 205

Ala Gly Glu Arg Arg Lys Gly Thr Asp Val Asn Val Phe Asn Thr Ile
    210                 215                 220

Leu Thr Thr Arg Ser Tyr Pro Gln Leu Arg Arg Val Phe Gln Lys Tyr
225                 230                 235                 240

Thr Lys Tyr Ser Lys His Asp Met Asn Lys Val Leu Asp Leu Glu Leu
                245                 250                 255

Lys Gly Asp Ile Glu Lys Cys Leu Thr Ala Ile Val Lys Cys Ala Thr
            260                 265                 270

Ser Lys Pro Ala Phe Phe Ala Glu Lys Leu His Gln Ala Met Lys Gly
        275                 280                 285

Val Gly Thr Arg His Lys Ala Leu Ile Arg Ile Met Val Ser Arg Ser
    290                 295                 300

Glu Ile Asp Met Asn Asp Ile Lys Ala Phe Tyr Gln Lys Met Tyr Gly
305                 310                 315                 320

Ile Ser Leu Cys Gln Ala Ile Leu Asp Glu Thr Lys Gly Asp Tyr Glu
                325                 330                 335

Lys Ile Leu Val Ala Leu Cys Gly Gly Asn
            340                 345

<210> SEQ ID NO 18
<211> LENGTH: 204
<212> TYPE: PRT
<213> ORGANISM: Homo sapiens -continued

```
<400> SEQUENCE: 18

Met Asn Leu Ile Leu Arg Tyr Thr Phe Ser Lys Met Ala Met Val Ser
1               5                   10                  15

Glu Phe Leu Lys Gln Ala Trp Phe Ile Glu Asn Glu Glu Gln Glu Tyr
                20                  25                  30

Val Gln Thr Val Lys Ser Ser Lys Gly Gly Pro Gly Ser Ala Val Ser
            35                  40                  45

Pro Tyr Pro Thr Phe Asn Pro Ser Ser Asp Val Ala Ala Leu His Lys
        50                  55                  60

Ala Ile Met Val Lys Gly Val Asp Glu Ala Thr Ile Ile Asp Ile Leu
65                  70                  75                  80

Thr Lys Arg Asn Asn Ala Gln Arg Gln Gln Ile Lys Ala Ala Tyr Leu
                85                  90                  95

Gln Glu Thr Gly Lys Pro Leu Asp Glu Thr Leu Lys Lys Ala Leu Thr
            100                 105                 110

Gly His Leu Glu Glu Val Val Leu Ala Leu Leu Lys Thr Pro Ala Gln
        115                 120                 125

Phe Asp Ala Asp Glu Leu Arg Ala Ala Met Lys Gly Leu Gly Thr Asp
    130                 135                 140

Glu Asp Thr Leu Ile Glu Ile Leu Ala Ser Arg Thr Asn Lys Glu Ile
145                 150                 155                 160

Arg Asp Ile Asn Arg Val Tyr Arg Glu Glu Leu Lys Arg Asp Leu Ala
                165                 170                 175

Lys Asp Ile Thr Ser Asp Thr Ser Gly Asp Phe Arg Asn Ala Leu Leu
            180                 185                 190

Ser Leu Ala Lys Gly Asp Arg Ser Glu Asp Phe Gly
        195                 200

<210> SEQ ID NO 19
<211> LENGTH: 115
<212> TYPE: PRT
<213> ORGANISM: Homo sapiens

<400> SEQUENCE: 19

Met Ala Met Val Ser Glu Phe Leu Lys Gln Ala Trp Phe Ile Glu Asn
1               5                   10                  15

Glu Glu Gln Glu Tyr Val Gln Thr Val Lys Ser Ser Lys Gly Gly Pro
                20                  25                  30

Gly Ser Ala Val Ser Pro Tyr Pro Thr Phe Asn Pro Ser Ser Asp Val
            35                  40                  45

Ala Ala Leu His Lys Ala Ile Met Val Lys Gly Val Asp Glu Ala Thr
        50                  55                  60

Ile Ile Asp Ile Leu Thr Lys Arg Asn Asn Ala Gln Arg Gln Gln Ile
65                  70                  75                  80

Lys Ala Ala Tyr Leu Gln Glu Thr Gly Lys Pro Leu Asp Glu Thr Leu
                85                  90                  95

Lys Lys Ala Leu Thr Gly His Leu Glu Glu Val Val Leu Ala Leu Leu
            100                 105                 110

Lys Thr Pro
        115

<210> SEQ ID NO 20
<211> LENGTH: 20
<212> TYPE: PRT
<213> ORGANISM: Artificial Sequence
<220> FEATURE:
```

<223> OTHER INFORMATION: Light chain signal sequence

<400> SEQUENCE: 20

Met Val Ser Ser Ala Gln Phe Leu Gly Leu Leu Leu Cys Phe Gln
1               5                   10                  15

Gly Thr Arg Cys
            20

<210> SEQ ID NO 21
<211> LENGTH: 19
<212> TYPE: PRT
<213> ORGANISM: Artificial Sequence
<220> FEATURE:
<223> OTHER INFORMATION: Heavy chain signal sequence

<400> SEQUENCE: 21

Met Gly Trp Thr Leu Val Phe Leu Phe Leu Leu Ser Val Thr Ala Gly
1               5                   10                  15

Val His Ser

<210> SEQ ID NO 22
<211> LENGTH: 239
<212> TYPE: PRT
<213> ORGANISM: Artificial Sequence
<220> FEATURE:
<223> OTHER INFORMATION: L1M2 light chain pro sequence

<400> SEQUENCE: 22

Met Val Ser Ser Ala Gln Phe Leu Gly Leu Leu Leu Cys Phe Gln
1               5                   10                  15

Gly Thr Arg Cys Asp Val Val Met Thr Gln Ser Pro Leu Ser Leu Pro
            20                  25                  30

Val Thr Leu Gly Gln Pro Ala Ser Ile Ser Cys Arg Ser Ser Gln Ser
        35                  40                  45

Leu Glu Asn Ser Asn Ala Lys Thr Tyr Leu Asn Trp Phe Gln Gln Arg
    50                  55                  60

Pro Gly Gln Ser Pro Arg Arg Leu Ile Tyr Gly Val Ser Asn Arg Phe
65                  70                  75                  80

Ser Gly Val Pro Asp Arg Phe Ser Gly Ser Gly Ser Gly Thr Asp Phe
                85                  90                  95

Thr Leu Lys Ile Ser Arg Val Glu Ala Glu Asp Val Gly Val Tyr Phe
            100                 105                 110

Cys Leu Gln Val Thr His Val Pro Tyr Thr Phe Gly Gln Gly Thr Lys
        115                 120                 125

Leu Glu Ile Lys Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys
225                 230                 235

<210> SEQ ID NO 23
<211> LENGTH: 467
<212> TYPE: PRT
<213> ORGANISM: Artificial Sequence
<220> FEATURE:
<223> OTHER INFORMATION: H4 heavy chain pro sequence

<400> SEQUENCE: 23

```
Met Gly Trp Thr Leu Val Phe Leu Phe Leu Leu Ser Val Thr Ala Gly
1               5                   10                  15

Val His Ser Gln Val Gln Leu Val Gln Ser Gly Ala Glu Val Lys Lys
            20                  25                  30

Pro Gly Ser Ser Val Lys Val Ser Cys Lys Ala Ser Gly Tyr Thr Phe
        35                  40                  45

Thr Asn Tyr Trp Ile Gly Trp Val Arg Gln Ala Pro Gly Gln Gly Leu
    50                  55                  60

Glu Trp Val Gly Asp Ile Tyr Pro Gly Gly Asp Tyr Thr Asn Tyr Asn
65                  70                  75                  80

Glu Lys Phe Lys Gly Arg Val Thr Ile Thr Ala Asp Lys Ser Thr Ser
                85                  90                  95

Thr Ala Tyr Met Glu Leu Ser Ser Leu Arg Ser Glu Asp Thr Ala Val
            100                 105                 110

Tyr Tyr Cys Ala Arg Trp Gly Leu Gly Tyr Tyr Phe Asp Tyr Trp Gly
        115                 120                 125

Gln Gly Thr Met Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Lys Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
        355                 360                 365
```

```
Tyr Thr Leu Pro Pro Ser Arg Asp Glu Leu Thr Lys Asn Gln Val Ser
        370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
                420                 425                 430

Asp Lys Ser Arg Trp Gln Gln Gly Asn Val Phe Ser Cys Ser Val Met
            435                 440                 445

His Glu Ala Leu His Asn His Tyr Thr Gln Lys Ser Leu Ser Leu Ser
        450                 455                 460

Pro Gly Lys
465

<210> SEQ ID NO 24
<211> LENGTH: 239
<212> TYPE: PRT
<213> ORGANISM: Artificial Sequence
<220> FEATURE:
<223> OTHER INFORMATION: L2M2 light chain pro sequence

<400> SEQUENCE: 24

Met Val Ser Ser Ala Gln Phe Leu Gly Leu Leu Leu Leu Cys Phe Gln
1               5                   10                  15

Gly Thr Arg Cys Asp Ile Val Met Thr Gln Thr Pro Leu Ser Leu Ser
            20                  25                  30

Val Thr Pro Gly Gln Pro Ala Ser Ile Ser Cys Arg Ser Ser Gln Ser
        35                  40                  45

Leu Glu Asn Ser Asn Ala Lys Thr Tyr Leu Asn Trp Tyr Leu Gln Lys
    50                  55                  60

Pro Gly Gln Ser Pro Gln Leu Leu Ile Tyr Gly Val Ser Asn Arg Phe
65                  70                  75                  80

Ser Gly Val Pro Asp Arg Phe Ser Gly Ser Gly Ser Gly Thr Asp Phe
                85                  90                  95

Thr Leu Lys Ile Ser Arg Val Glu Ala Glu Asp Val Gly Val Tyr Tyr
            100                 105                 110

Cys Leu Gln Val Thr His Val Pro Tyr Thr Phe Gly Gln Gly Thr Lys
        115                 120                 125

Val Glu Ile Lys Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys
225                 230                 235

<210> SEQ ID NO 25
```

<211> LENGTH: 467
<212> TYPE: PRT
<213> ORGANISM: Artificial Sequence
<220> FEATURE:
<223> OTHER INFORMATION: H2 heavy chain pro sequence

<400> SEQUENCE: 25

```
Met Gly Trp Thr Leu Val Phe Leu Phe Leu Leu Ser Val Thr Ala Gly
1               5                   10                  15

Val His Ser Gln Val Gln Leu Val Gln Ser Gly Pro Glu Val Lys Lys
            20                  25                  30

Pro Gly Glu Ser Leu Lys Ile Ser Cys Lys Gly Ser Gly Tyr Thr Phe
        35                  40                  45

Thr Asn Tyr Trp Ile Gly Trp Val Arg Gln Ala Pro Gly Lys Gly Leu
    50                  55                  60

Glu Trp Met Gly Asp Ile Tyr Pro Gly Gly Asp Tyr Thr Asn Tyr Asn
65                  70                  75                  80

Glu Lys Phe Lys Gly Gln Val Thr Ile Ser Ala Asp Lys Ser Ile Ser
                85                  90                  95

Thr Ala Tyr Leu Gln Trp Ser Ser Leu Lys Ala Ser Asp Thr Ala Ile
            100                 105                 110

Tyr Tyr Cys Ala Arg Trp Gly Leu Gly Tyr Tyr Phe Asp Tyr Trp Gly
        115                 120                 125

Arg Gly Thr Leu Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Lys Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Asp Glu Leu Thr Lys Asn Gln Val Ser
    370                 375                 380
```

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
            405                 410                 415

Val Leu Asp Ser Asp Gly Ser Phe Phe Leu Tyr Ser Lys Leu Thr Val
        420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
    450                 455                 460

Pro Gly Lys
465

<210> SEQ ID NO 26
<211> LENGTH: 720
<212> TYPE: DNA
<213> ORGANISM: Artificial Sequence
<220> FEATURE:
<223> OTHER INFORMATION: L1M2 light chain pro sequence

<400> SEQUENCE: 26
atggtgtcat ccgctcaatt tctcggtttg cttctcctgt gtttccaagg cacccgctgc     60
gacgtggtca tgacccagag cccactgagc cttccggtca ccttgggaca gcccgcctca    120
atttcatgcc ggtccagcca gtccctggag aactccaacg ccaagaccta tctgaactgg    180
ttccagcagc gccctggaca gtccccgagg cgcctgatct acggcgtcag caacaggttc    240
tcgggcgtgc cggacagatt ctccggctcc ggaagcggaa ctgacttcac cctgaaaatc    300
tcaagagtgg aagccgagga cgtgggcgtg tacttctgcc tccaagtcac gcacgtgccg    360
tacactttcg gacaagggac taagctggag atcaagcgga ccgtggcggc ccctctgtg    420 ttcatttttcc ctccctcgga cgaacagctg aagtcgggaa cagcctccgt cgtgtgcctg    480
ctcaacaact tctaccccccg ggaagcgaag gtccagtgga agtggataa cgcactccaa    540 tcggggaact cccaggaatc cgtgactgag caggactcga aggattccac ttactccctg    600
tcgtccaccc tgactctgag caaggccgac tacgagaagc ataaggtcta cgcctgcgaa    660
gtgacccacc agggtctgag ctcccctgtg accaagagct taatcgggg cgaatgttga    720

<210> SEQ ID NO 27
<211> LENGTH: 1404
<212> TYPE: DNA
<213> ORGANISM: Artificial Sequence
<220> FEATURE:
<223> OTHER INFORMATION: H4 heavy chain pro sequence

<400> SEQUENCE: 27
atgggatgga ctctcgtgtt ccttttttctc ctctctgtca ctgccggggt gcattcgcaa     60
gtccagctgg tgcagtcggg agcagaggtg aaaaagcccg gatcgtcagt gaaggtcagc    120
tgcaaagcct cggatacac tttcaccaac tactggattg gatgggtcag acaggcccccc    180 ggccaaggac tggagtgggt cggcgacatc taccctgggg gcgactatac caactacaac    240
gaaaagttca aggacgcgt gacaattacc gccgataaga gcaccagcac tgcctacatg    300
gagcttagct cattgcggtc cgaggatacc gctgtgtact actgtgcgcg gtggggcctt    360
ggttactact cgactactg gggacagggt accatggtca cggtgtcctc gcgtccaccc    420 aagggtcccct ccgtgttccc tctcgcgccg tcctcaaagt ctacctccgg tggaactgcc    480

| | |
|---|---|
| gcgctcggtt gtctcgtgaa ggactacttc ccggagcctg tgactgtctc ctggaactcc | 540 |
| ggggcccctca ccagcggagt gcacactttc ccgccgtgc tgcaatcctc cggcctgtac | 600 |
| agcctgtcct ccgtcgtgac tgtgcctagc tcctccctgg aacccagac ctacatctgc | 660 |
| aacgtgaacc acaagccctc caacaccaag gtcgacaaga aggtcgaacc gaagtcgtgc | 720 |
| gacaagactc atacgtgccc tccttgcccg gccccggaac tgctgggagg cccatccgtg | 780 |
| ttcctgttcc cacccaagcc taaggatacc ctgatgatca gcagaacacc ggaagtgacc | 840 |
| tgtgtggtgg tggacgtcag ccacgaagat cccgaggtca agttcaattg gtacgtggac | 900 |
| ggggtggagg tgcacaacgc aaagaccaag ccccgggagg aacagtacaa ctccacctat | 960 |
| cgcgtggtgt cggtgctgac ggtgctgcac caggactggt tgaacggaaa ggagtataag | 1020 |
| tgcaaagtgt cgaacaaggc cctgcccgct cctatcgaaa agaccatctc caaggccaag | 1080 |
| ggccagccgc gggaacccca ggtctacact ctcccaccga gccgcgacga actgactaag | 1140 |
| aatcaagtgt cgctgacttg cctcgtcaag ggcttctacc cgtccgacat cgccgtggaa | 1200 |
| tgggagagca acggccagcc ggaaaacaac tacaagacca cccctcccgt gctggattcc | 1260 |
| gacgggtcct tcttcctgta ctcaaaactg accgtggata gtccagatg gcagcagggc | 1320 |
| aatgtctttt catgctccgt gatgcacgag gctctgcata accactacac ccagaagtcg | 1380 |
| ctgtccctgt ccccggggaa gtga | 1404 |

<210> SEQ ID NO 28
<211> LENGTH: 720
<212> TYPE: DNA
<213> ORGANISM: Artificial Sequence
<220> FEATURE:
<223> OTHER INFORMATION: L2M2 light chain pro sequence

<400> SEQUENCE: 28

| | |
|---|---|
| atggtgtcat ccgctcaatt tctcggtttg cttctcctgt gtttccaagg cacccgctgc | 60 |
| gacatcgtca tgacccagac cccattgagc ctttccgtca cgccgggaca gcccgcctcc | 120 |
| atttcctgcc gctcaagcca gtccctggag aactcaaacg ccaagaccta cctgaattgg | 180 |
| tatctgcaga agcctggaca gagcccgcag ctgctgatct acggcgtcag caacaggttc | 240 |
| tcgggcgtgc cggacagatt ctccggctcc ggaagcggaa ctgacttcac cctgaaaatc | 300 |
| tcacgcgtgg aagccgagga cgtgggcgtg tactactgcc tccaagtcac ccacgtgccg | 360 |
| tacactttcg gacaagggac taaggtcgag atcaagcgga ccgtggcggc cccctctgtg | 420 |
| ttcattttcc ctccctcgga cgaacagctg aagtcgggaa cagcctccgt cgtgtgcctg | 480 |
| ctcaacaact tctacccccg ggaagcgaag gtccagtgga aagtggataa cgcactccaa | 540 |
| tcggggaact cccaggaatc cgtgactgag caggactcga aggattccac ttactccctg | 600 |
| tcgtccaccc tgactctgag caaggccgac tacgagaagc ataaggtcta cgcctgcgaa | 660 |
| gtgacccacc agggtctgag ctcccctgtg accaagagct taatcgggg cgaatgttga | 720 |

<210> SEQ ID NO 29
<211> LENGTH: 1404
<212> TYPE: DNA
<213> ORGANISM: Artificial Sequence
<220> FEATURE:
<223> OTHER INFORMATION: H2 heavy chain pro sequence

<400> SEQUENCE: 29

| | |
|---|---|
| atgggatgga ctctcgtgtt cctttttctc ctctctgtca ctgccggggt gcattcgcaa | 60 |
| gtccagctgg tgcagtcggg accagaggtg aaaaagcccg agagtcact taagatcagc | 120 |

```
tgcaaaggct cgggatacac tttcaccaac tactggattg gttgggtcag acaggccccc      180
ggcaaaggac tggagtggat gggcgacatc taccctgggg gcgactatac caactacaac      240
gaaaagttca agggacaagt gacaatttcg ccgataaga gcattagcac tgcatacctt       300
cagtggagct cattgaaggc ctccgatacc gctatctact actgtgcgcg gtggggcctg      360
ggatactact tcgactactg gggaaggggt accttggtca cggtgtcctc cgcgtccacc      420
aagggtccct ccgtgttccc tctcgcgccg tcctcaaagt ctacctccgg tggaactgcc      480
gcgctcggtt gtctcgtgaa ggactacttc ccggagcctg tgactgtctc ctggaactcc      540
ggggccctca ccagcggagt gcacactttc cccgccgtgc tgcaatcctc cggcctgtac      600
agcctgtcct ccgtcgtgac tgtgcctagc tcctccctgg aacccagac ctacatctgc       660 aacgtgaacc acaagccctc caacaccaag gtcgacaaga aggtcgaacc gaagtcgtgc      720
gacaagactc atacgtgccc tccttgcccg gccccggaac tgctgggagg cccatccgtg      780
ttcctgttcc cacccaagcc taaggatacc ctgatgatca gcagaacacc ggaagtgacc      840
tgtgtggtgg tggacgtcag ccacgaagat cccgaggtca agttcaattg gtacgtggac      900
ggggtggagg tgcacaacgc aaagaccaag ccccgggagg aacagtacaa ctccacctat      960
cgcgtggtgt cggtgctgac ggtgctgcac caggactggt tgaacggaaa ggagtataag     1020
tgcaaagtgt cgaacaaggc cctgccggct cctatcgaaa agaccatctc caaggccaag     1080
ggccagccgc gggaacccca ggtctacact ctcccaccga gccgcgacga actgactaag     1140
aatcaagtgt cgctgacttg cctcgtcaag ggcttctacc cgtccgacat cgccgtggaa     1200
tgggagagca acggccagcc ggaaaacaac tacaagacca cccctcccgt gctggattcc     1260
gacgggtcct tcttcctgta ctcaaaactg accgtggata agtccagatg gcagcagggc     1320
aatgtctttt catgctccgt gatgcacgag gctctgcata accactacac ccagaagtcg     1380
ctgtccctgt ccccggggaa gtga                                            1404

<210> SEQ ID NO 30
<211> LENGTH: 22
<212> TYPE: PRT
<213> ORGANISM: Homo sapiens

<400> SEQUENCE: 30

Met Val Ser Glu Phe Leu Lys Gln Ala Trp Phe Ile Glu Asn Glu Glu
1               5                   10                  15

Gln Glu Tyr Val Gln Thr
            20

<210> SEQ ID NO 31
<211> LENGTH: 25
<212> TYPE: PRT
<213> ORGANISM: Homo sapiens

<400> SEQUENCE: 31

Ala Met Val Ser Glu Phe Leu Lys Gln Ala Trp Phe Ile Glu Asn Glu
1               5                   10                  15

Glu Gln Glu Tyr Val Gln Thr Val Lys
            20                  25
```

CANCER TREATMENT WITH AN ANTIBODY

SEQUENCE LISTING

A sequence listing in electronic (ASCII text file) format is filed with this application and incorporated herein by reference. The name of the ASCII text file is "Sequence_Listing_0136.txt"; the file was created on Feb. 4, 2021; the size of the file is 43,967 bytes.

The present invention provides a specific binding molecule for use in the treatment of cancer in a subject. The specific binding molecule binds human annexin-A1 (Anx-A1), and in particular embodiments is an antibody or antibody fragment.

Cancer is a group of diseases characterised by abnormal cell growth. Characteristically, the abnormal cell growth associated with cancer results in the formation of a tumour (a solid mass of cells formed due to abnormal cell growth), though this is not always the case (particularly in cancers of the blood). In 2010 (the most recent year for which detailed statistics are available), across the world more people (about 8 million) died from cancer than any other single cause (Lozano et al., Lancet 380: 2095-2128, 2012). Furthermore, as populations across the world age, cancer rates are expected to increase. There is thus an urgent need for new and improved therapies for cancer.

Moreover, many cancer deaths are a result of a cancer becoming resistant to chemotherapy drugs. Methods by which cancers become drug-resistant are reviewed in Housman et al. (*Cancers* 6: 1769-1792, 2014). As detailed therein, cancers may become drug-resistant by a variety of different mechanisms, including inactivation or metabolism of drugs (or the prevention of their metabolic activation), mutation or alteration of drug target and drug efflux via ABC transporters. Such mechanisms can result in cancers becoming multidrug resistant (MDR). As discussed below, drug resistance is a particular problem for therapy with platinum-based chemotherapy agents.

Platinum-based chemotherapy agents are a common first-line treatment option in several different cancers, including testicular cancer, ovarian cancer, colorectal cancer, cervical cancer, breast cancer, bladder cancer, head and neck cancers, oesophageal cancer, lung cancer, mesothelioma, lymphoma, brain tumours and neuroblastoma. Platinum-based chemotherapy agents include cisplatin, oxaliplatin and carboplatin. All platinum-based chemotherapy agents work in essentially the same way, by reacting with the N-7 position at guanine residues to form inter- and intrastrand DNA crosslinks and DNA-protein crosslinks. The crosslinks inhibit DNA synthesis and/or repair, and cause initiation of apoptosis (Shen et al., *Pharmacol. Rev.* 64: 706-721, 2012). However, while patients generally initially respond well to platinum-based chemotherapy, the large majority then relapse due to the development of resistance to the treatment (particularly in the case of cisplatin), resulting in treatment failure (Shen et al., supra). Thus the development of resistance to platinum-based therapies is a significant challenge in oncology today. Cancers develop resistance to platinum-based therapies via a number of mechanisms, including reduction of accumulation of platinum-based chemotherapy agents in target cells (due to reduced influx and/or increased efflux) and (re-) activation of DNA repair pathways.

Thus the development of resistance to platinum-based therapies is a significant challenge in oncology today. New treatment options for cancers that are or have become resistant to traditional chemotherapeutics (particularly platinum-based chemotherapeutics) are urgently needed.

The present inventors have discovered that particular specific binding molecules (e.g. antibodies) against Anx-A1 are effective in treating cancer. The molecules have been found to be particularly effective in treating drug-resistant cancer, including cancer that is resistant to platinum-based chemotherapy. The present invention thus provides a new treatment option for cancer patients, particularly for patients with cancer that is resistant to chemotherapy agents. Such a treatment option answers an urgent need for new therapies for individuals whose disease is unresponsive to traditional chemotherapy.

The specific binding molecules of the invention have been found to be effective in the treatment of a wide variety of cancers, including breast cancer, colorectal cancer, ovarian cancer, lung cancer and pancreatic cancer.

Breast cancer is the most common cancer among women, and causes more deaths in women worldwide than any other cancer (Becker, *Int J Gynaecol Obstet* 131 (2015), S36-S39). Over 55,000 cases of breast cancer are diagnosed each year in the UK (and over 300 cases in men). Although the mortality rate for breast cancer is lower than for many other cancers, in the UK over 11,000 deaths annually are caused by breast cancer. Breast cancer lacking expression of the oestrogen receptor, progesterone receptor and the hormone epidermal growth factor receptor HER2 (known as triple negative breast cancer) is particularly difficult to treat, since many modern breast cancer drugs target these receptors. The specific binding molecules of the invention have been found to be effective in treating breast cancer, including triple negative breast cancer, providing an important new treatment option for this disease.

Ovarian cancer is another cancer common in women, which is difficult to treat. In the UK alone there are over 7,500 incidences of ovarian cancer every year, resulting in over 4,000 deaths (ovarian cancer is frequently diagnosed at a late stage, resulting in this relatively low survival rate). Pancreatic cancer is relatively common, with over 9,000 cases each year in the UK alone, but it is known to be one of the most untreatable cancers, with a survival rate of less than 1% (again, this is primarily due to the disease being diagnosed at a late stage). The specific binding molecules of the invention have been found to be effective in treating both of these cancers, providing a much-needed new therapy for cancers that are hard to treat. Colorectal (or bowel) cancer is also a common cancer with 42,000 cases diagnosed in the UK each year. Despite being only the fourth most common cancer in the UK it is the second most common cancer resulting in death. Similarly, lung cancer is diagnosed in over 47,000 individuals each year in the UK with only 5% surviving for ten years or more after diagnosis. The specific binding molecules of the invention offer useful new therapies for these cancers.

Full length human Anx-A1 has the amino acid sequence set forth in SEQ ID NO: 17. Anx-A1 is a member of the annexin protein family. Most proteins of this family, including Anx-A1, are characterised by the presence of a "core" region comprising four, homologous, repeating domains, each of which comprises at least one $Ca^2$-binding site. Each member of the family is distinguished by a unique N-terminal region. Anx-A1 is a monomeric amphipathic protein, predominantly located in the cytoplasm of cells in which it is expressed. However, Anx-A1 can also be exported, resulting in cell surface localisation (D'Acquisto et al., *Br. J. Pharmacol.* 155: 152-169, 2008).

Anx-A1 is known to play a role in regulation of the immune system, being involved in the homeostasis of various cell types of both the innate and adaptive immune systems. For instance, Anx-A1 has been shown to exert homeostatic control over cells of the innate immune system such as neutrophils and macrophages, and also to play a role in T-cells by modulating the strength of T-cell receptor (TCR) signalling (D'Acquisto et al., Blood 109: 1095-1102, 2007). Use of a neutralising antibody against Anx-A1 to inhibit its roles in the adaptive immune system has been shown to be effective in the treatment of various T-cell-mediated diseases, including autoimmune diseases such as rheumatoid arthritis and multiple sclerosis (WO 2010/064012; WO 2011/154705).

Antibodies against Anx-A1 have also been shown to be useful in the treatment of certain psychiatric conditions, in particular anxiety, obsessive-compulsive disorder (OCD) and related diseases (WO 2013/088111), though the mechanism by which this occurs is unknown.

WO 2005/027965 demonstrates that Anx-A1 is localised to the surface of apoptotic cells, and that anti-Anx-A1 antibodies can be used to monitor apoptosis. The document teaches that on this basis such antibodies may thus be used to monitor and diagnose cancer. The document also teaches that Anx-A1 expression on the surface of apoptotic cells inhibits an immune response against the cells. On this basis, the document speculates that an antibody that binds Anx-A1 can be used to treat cancer, by blocking the immunosuppressant effect of Anx-A1 on cells that have commenced apoptosis and thus stimulating an immune response against the cancer.

Oh et al. (Nature 429: 629-635, 2004) teaches that Anx-A1 is expressed on some solid tumours and may be used as a target to direct radioimmunotherapy to those cancers, and demonstrates that such therapy enhances survival in an animal model of disease. US 2015/0086553 suggests that anti-Anx-A1 antibodies can be used in cancer treatment and diagnosis but fails to teach how such treatment might be performed. The binding of an anti-Anx-A1 scFv to the gastric cancer cell line SNU-1 is demonstrated. Wang et al. (Biochem. BioPhys. Res. Commun. 314: 565-570, 2004) demonstrates a correlation between Anx-A1 expression and multi-drug resistance in cancer. Thus several diseases have been shown to display an association with Anx-A1 expression, including cancer. However, prior to the present invention it had not been demonstrated that an anti-Anx-A1 antibody, particularly when used without any co-treatment, could be used to treat cancer.

Indeed, the present invention demonstrates that efficacy in the treatment of cancer does not extend to all specific binding molecules which bind human Anx-A1. The present invention provides particular specific binding molecules which bind human Anx-A1 and can advantageously be used to treat cancer, particularly cancer which is resistant to chemotherapy drugs and/or breast cancer, colorectal cancer, ovarian cancer, lung cancer and pancreatic cancer. It is unknown why the specific binding molecules of the invention are effective in cancer treatment, while other specific binding molecules that also bind human Anx-A1 are not. Without being bound by theory, it is speculated that the activity of specific binding molecules that bind human Anx-A1 may be dependent on the epitope recognised.

A number of monoclonal antibodies that recognise human Anx-A1 are disclosed in WO 2018/146230. The antibodies disclosed in WO 2018/146230 have particularly advantageous properties, in that they are able to bind to human Anx-A1 with very high affinity. It has now been discovered by the inventors that the antibodies disclosed in WO 2018/146230 are useful in treating cancer, as described further below.

Thus in a first aspect the invention provides a specific binding molecule which binds human Anx-A1 for use in the treatment of cancer in a subject, wherein:

(i) said specific binding molecule comprises the complementarity-determining regions (CDRs) VLCDR1, VLCDR2, VLCDR3, VHCDR1, VHCDR2 and VHCDR3, each of said CDRs having an amino acid sequence as follows:

VLCDR1 has the sequence set forth in SEQ ID NO: 1, 7 or 8;
VLCDR2 has the sequence set forth in SEQ ID NO: 2;
VLCDR3 has the sequence set forth in SEQ ID NO: 3;
VHCDR1 has the sequence set forth in SEQ ID NO: 4;
VHCDR2 has the sequence set forth in SEQ ID NO: 5; and
VHCDR3 has the sequence set forth in SEQ ID NO: 6; or,
for each sequence, an amino acid sequence with at least 85% sequence identity thereto; and/or (ii) said specific binding molecule binds to Anx-A1 at a discontinuous epitope consisting of amino acids 197-206, 220-224 and 227-237 of SEQ ID NO: 17.

Similarly, the invention provides a method of treating cancer in a subject, comprising administering to said subject a specific binding molecule as defined above. Also provided is the use of a specific binding molecule as defined above in the manufacture of a medicament for the treatment of cancer in a subject.

In a second aspect, the invention provides a kit comprising a specific binding molecule as defined above and a chemotherapeutic agent.

In a third aspect, the invention provides a product comprising a specific binding molecule as defined above and a second therapeutic agent for separate, simultaneous or sequential use in the treatment of cancer in a subject.

As mentioned above, the invention provides a specific binding molecule which binds human Anx-A1 for use in the treatment of cancer in a subject. A "specific binding molecule" as defined herein is a molecule that binds specifically to a particular molecular partner, in this case human Anx-A1. A molecule that binds specifically to human Anx-A1 is a molecule that binds to human Anx-A1 with a greater affinity than that with which it binds to other molecules, or at least most other molecules. Thus, for example, if a specific binding molecule that binds human Anx-A1 were contacted with a lysate of human cells, the specific binding molecule would bind primarily to Anx-A1. In particular, the specific binding molecule binds to a sequence or configuration present on said human Anx-A1. When the specific binding molecule is an antibody the sequence or configuration is the epitope to which the specific binding molecule binds. The Anx-A1 epitope bound by the specific binding molecules for use according to the invention is described below.

The specific binding molecule for use herein does not necessarily bind only to human Anx-A1: the specific binding molecule may cross-react with certain other undefined target molecules, or may display a level of non-specific binding when contacted with a mixture of a large number of molecules (such as a cell lysate or suchlike). For instance, the specific binding molecule may display a level of cross-reactivity with other members of the human annexin family, and/or with Anx-A1 proteins from other animals. Regardless, a specific binding molecule for use according to the invention shows specificity for Anx-A1. The skilled person will easily be able to identify whether a specific binding molecule shows specificity for Anx-A1 using standard techniques in the art, e.g. ELISA, Western-blot, surface plasmon resonance (SPR), etc. In particular embodiments, the specific binding molecule for use herein binds human Anx-A1 with a $K_D$ (dissociation constant) of less than 20 nM, 15 nM or 10 nM. In a preferred embodiment, the specific binding molecule for use herein binds human Anx-A1 with a $K_D$ of less than 5 nM.

The $K_D$ of the binding of the specific binding molecule to Anx-A1 is preferably measured under binding conditions in which $Ca^{2+}$ ions are present at a concentration of at least 1 mM, and optionally HEPES is present at a concentration of from 10-20 mM, and the pH is between 7 and 8, preferably of a physiological level between 7.2 and 7.5 inclusive. NaCl may be present, e.g. at a concentration of from 100-250 mM, and a low concentration of a detergent, e.g. polysorbate 20, may also be present. Such a low concentration may be e.g. from 0.01 to 0.5% v/v. A number of methods by which the $K_D$ of an interaction between a specific binding molecule and its ligand may be calculated are well known in the art. Known techniques include SPR (e.g. Biacore) and polarization-modulated oblique-incidence reflectivity difference (OI-RD).

As described above, a molecule that "binds to human Anx-A1" shows specificity for a human Anx-A1 molecule. There are three human isoforms of human Anx-A1, obtained from translation of four alternatively-spliced Anx-A1 mRNAs. The full-length human Anx-A1 protein is obtained from translation of the ANXA1-002 or ANXA1-003 transcript, and as noted above has the amino acid sequence set forth in SEQ ID NO: 17. The ANXA1-004 and ANXA1-006 transcripts encode fragments of the full-length human Anx-A1 protein, which respectively have the amino acid sequences set forth in SEQ ID NOs: 18 and 19.

The specific binding molecule for use according to the invention binds to full-length human Anx-A1 (i.e. Anx-A1 of SEQ ID NO: 17, encoded by the ANXA1-002 or ANXA1-003 transcript, which is a 346 amino acid protein). The specific binding molecule may also bind to particular fragments, parts or variants of full-length Anx-A1, such as the fragments encoded by the ANXA1-004 and ANXA1-006 transcripts.

As discussed hereinafter, antibodies (and molecules containing CDRs) form preferred specific binding molecules for use according to the invention.

As mentioned above, a number of monoclonal antibodies that recognise human Anx-A1 are disclosed in WO 2018/146230. As is known to the skilled person, antibodies are proteins that comprise four polypeptide chains: two heavy chains and two light chains. Typically, the heavy chains are identical to each other and the light chains are identical to each other. The light chains are shorter (and thus lighter) than the heavy chains. The heavy chains comprise four or five domains: at the N-terminus a variable ($V_H$) domain is located, followed by three or four constant domains (from N-terminus to C-terminus $C_H1$, $C_H2$, $C_H3$ and, where present, $C_H4$, respectively). The light chains comprise two domains: at the N-terminus a variable ($V_L$) domain is located and at the C-terminus a constant ($C_L$) domain is located. In the heavy chain an unstructured hinge region is located between the $C_H1$ and $C_H2$ domains. The two heavy chains of an antibody are joined by disulphide bonds formed between cysteine residues present in the hinge region, and each heavy chain is joined to one light chain by a disulphide bond between cysteine residues present in the $C_H1$ and $C_L$ domains, respectively.

In mammals, two types of light chain are produced, known as lambda (λ) and kappa (κ). For kappa light chains, the variable and constant domains can be referred to as $V_K$ and $C_K$ domains, respectively. Whether a light chain is a λ or κ light chain is determined by its constant region: the constant regions of λ and κ light chains differ, but are the same in all light chains of the same type in any given species.

The constant regions of the heavy chains are the same in all antibodies of any given isotype in a species, but differ between isotypes (examples of antibody isotypes are classes IgG, IgE, IgM, IgA and IgD; there are also a number of antibody sub-types, e.g. there are four sub-types of IgG antibodies: IgG1, IgG2, IgG3 and IgG4). The specificity of an antibody is determined by the sequence of its variable region. The sequence of variable regions varies between antibodies of the same type in any individual. In particular, both the light and heavy chains of an antibody comprise three hypervariable complementarity-determining regions (CDRs). In a pair of a light chain and a heavy chain, the CDRs of the two chains form the antigen-binding site. The CDR sequences determine the specificity of an antibody.

The three CDRs of a heavy chain are known as VHCDR1, VHCDR2 and VHCDR3, from N-terminus to C-terminus, and the three CDRs of a light chain are known as VLCDR1, VLCDR2 and VLCDR3, from N-terminus to C-terminus. One antibody disclosed in WO 2018/146230 has the following CDR sequences:

VLCDR1: RSSQSLENSNAKTYLN (SEQ ID NO: 1);
VLCDR2: GVSNRFS (SEQ ID NO: 2);
VLCDR3: LQVTHVPYT (SEQ ID NO: 3);
VHCDR1: GYTFTNYWIG (SEQ ID NO: 4);
VHCDR2: DIYPGGDYTNYNEKFKG (SEQ ID NO: 5); and
VHCDR3: ARWGLGYYFDY (SEQ ID NO: 6).

Another antibody disclosed in WO 2018/146230 has the following CDR sequences:

VLCDR1: RSSQSLENSNGKTYLN (SEQ ID NO: 7);
VLCDR2: GVSNRFS (SEQ ID NO: 2);
VLCDR3: LQVTHVPYT (SEQ ID NO: 3);
VHCDR1: GYTFTNYWIG (SEQ ID NO: 4);
VHCDR2: DIYPGGDYTNYNEKFKG (SEQ ID NO: 5); and
VHCDR3: ARWGLGYYFDY (SEQ ID NO: 6).

Another antibody disclosed in WO 2018/146230 has the following CDR sequences:

VLCDR1: RSSQSLENTNGKTYLN (SEQ ID NO: 8);
VLCDR2: GVSNRFS (SEQ ID NO: 2);
VLCDR3: LQVTHVPYT (SEQ ID NO: 3);
VHCDR1: GYTFTNYWIG (SEQ ID NO: 4);
VHCDR2: DIYPGGDYTNYNEKFKG (SEQ ID NO: 5); and
VHCDR3: ARWGLGYYFDY (SEQ ID NO: 6).

Thus the antibodies disclosed in WO 2018/146230 have identical CDR sequences, save for the VLCDR1 sequences. The VLCDR1 sequence of SEQ ID NO: 7 is a wild-type VLCDR1 sequence, found in the murine antibody Mdx001 which was constructed from a minor mRNA sequence obtained from the hybridoma deposited with the ECACC having accession number 10060301. Humanised versions of Mdx001 were generated and, surprisingly, modification of the VLCDR1 sequence in these humanised antibodies was found to yield enhanced antibodies. Substitution of the glycine residue at position 11 of SEQ ID NO: 7 enhances antibody stability and function. Without being bound by theory it is believed that this is achieved by removing a site for post-translational modification of the CDR. Specifically, it is believed that substitution of this glycine residue removes a deamidation site from the protein. The VLCDR1 sequence set forth in SEQ ID NO: 7 comprises the sequence motif Ser-Asn-Gly. This sequence motif is associated with deamidation of the Asn residue, which leads to conversion of the asparagine residue to aspartic acid or isoaspartic acid, which can affect antibody stability and target binding. Substitution of any one of the residues within the Ser-Asn-Gly motif is believed to remove the deamidation site.

The inventors identified antibodies in which the glycine residue at position 11 of SEQ ID NO: 7 (which is the glycine residue located within the above-described deamidation site) is substituted for alanine and which display enhanced binding to their target (Anx-A1) relative to the native, Mdx001 antibody. The VLCDR1 comprising the substitution of glycine at position 11 for alanine has the amino acid sequence RSSQSLENSNAKTYLN (the residue in bold is the alanine introduced by the aforementioned substitution), which is set forth in SEQ ID NO: 1. Further, humanised antibodies comprising a VLCDR1 modified at position 9, by substitution of serine for threonine, were also found to display enhanced binding of Anx-A1 relative to Mdx001. The VLCDR1 comprising the substitution of serine at position 9 for threonine has the amino acid sequence RSSQSLENTNGKTYLN (the residue in bold is the threonine introduced by the aforementioned substitution), which is set forth in SEQ ID NO: 8. As mentioned above, the inventors have discovered that the antibodies disclosed in WO 2018/146230 are suitable for use in therapy for cancer.

The antibodies disclosed in WO 2018/146230 were generated by genetic immunisation of a mouse with human Anx-A1, meaning the mouse's immune system was exposed to whole, intact human Anx-A1 in its native conformation. As detailed in the examples, analysis of the antibodies of WO 2018/146230 by hydrogen-deuterium exchange (HDX) demonstrated that they bind human Anx-A1 at a discontinuous epitope consisting of amino acids 197-206, 220-224 and 227-237 of human Anx-A1 (that is to say, amino acids 197-206, 220-224 and 227-237 of SEQ ID NO: 17).

Notably, the antibodies of WO 2018/146230 bind Anx-A1 only in the presence of physiological concentrations of $Ca^{2+}$. Without being bound by theory, it is believed that this is a result of the location of their epitope on the Anx-A1 molecule. In the absence of $Ca^{2+}$, its N-terminus sits in a "pocket" located adjacent to this discontinuous epitope. Binding of $Ca^{2+}$ to Anx-A1 (which occurs under physiological $Ca^{2+}$ concentrations) results in a change of conformation of Anx-A1 leading to expulsion of the N-terminus from its pocket in the core domain, which is believed to expose the epitope, allowing the antibody to bind. Any antibody (or similar specific binding molecule) which binds this epitope of Anx-A1 may be used in methods and uses described herein.

The specific binding molecule for use according to the present invention may comprise the CDR sequences of any of the three antibodies disclosed in WO 2018/146230, or variants thereof. Alternatively or additionally, the specific binding molecule for use according to the invention may bind Anx-A1 at the same epitope as the antibodies of WO 2018/146230. Accordingly, the specific binding molecule for use according to the present invention:
(i) comprises the complementarity-determining regions (CDRs) VLCDR1, VLCDR2, VLCDR3, VHCDR1, VHCDR2 and VHCDR3, each of said CDRs having an amino acid sequence as follows:
VLCDR1 has the sequence set forth in SEQ ID NO: 1, 7 or 8;
VLCDR2 has the sequence set forth in SEQ ID NO: 2;
VLCDR3 has the sequence set forth in SEQ ID NO: 3;
VHCDR1 has the sequence set forth in SEQ ID NO: 4;
VHCDR2 has the sequence set forth in SEQ ID NO: 5; and
VHCDR3 has the sequence set forth in SEQ ID NO: 6; or, for each sequence, an amino acid sequence with at least 85%, 90% or 95% sequence identity thereto; and/or
(ii) binds to human Anx-A1 at a discontinuous epitope consisting of amino acids 197-206, 220-224 and 227-237 of SEQ ID NO: 17.

In a preferred aspect the specific binding molecules of (i) bind to the epitope as described in (ii).

By "or, for each sequence, an amino acid sequence with at least 85%, 90% or 95% sequence identity thereto" is meant that each of the said CDRs may have the amino acid sequence specified in the relevant SEQ ID NO, or an amino acid sequence with at least 85%, 90% or 95% sequence identity thereto. Thus VLCDR1 has the sequence set forth in SEQ ID NO: 1, 7 or 8, or an amino acid sequence with at least 85%, 90% or 95% sequence identity to SEQ ID NO: 1, 7 or 8; VLCDR2 has the sequence set forth in SEQ ID NO: 2, or an amino acid sequence with at least 85%, 90% or 95% sequence identity to SEQ ID NO: 2; VLCDR3 has the sequence set forth in SEQ ID NO: 3, or an amino acid sequence with at least 85%, 90% or 95% sequence identity to SEQ ID NO: 3; VHCDR1 has the sequence set forth in SEQ ID NO: 4, or an amino acid sequence with at least 85%, 90% or 95% sequence identity to SEQ ID NO: 4; VHCDR2 has the sequence set forth in SEQ ID NO: 5, or an amino acid sequence with at least 85%, 90% or 95% sequence identity to SEQ ID NO: 5; and VHCDR3 has the sequence set forth in SEQ ID NO: 6, or an amino acid sequence with at least 85%, 90% or 95% sequence identity to SEQ ID NO: 6. An amino acid sequence with at least 85%, 90% or 95% sequence identity (but less than 100% sequence identity) to a particular SEQ ID NO is known herein as a variant of that SEQ ID NO, e.g. an amino acid sequence having at least 85% sequence identity to SEQ ID NO: 1, but less than 100% sequence identity to SEQ ID NO: 1, is a variant of SEQ ID NO: 1.

In a particular embodiment, the specific binding molecule for use according to the invention comprises CDRs having the following amino acid sequences:
VLCDR1 has the sequence set forth in SEQ ID NO: 1;
VLCDR2 has the sequence set forth in SEQ ID NO: 2;
VLCDR3 has the sequence set forth in SEQ ID NO: 3;
VHCDR1 has the sequence set forth in SEQ ID NO: 4;
VHCDR2 has the sequence set forth in SEQ ID NO: 5; and
VHCDR3 has the sequence set forth in SEQ ID NO: 6.

As indicated, the specific binding molecule for use according to the invention may comprise 6 CDRs consisting of polypeptide sequences. As used herein, "protein" and "polypeptide" are interchangeable, and each refers to a sequence of 2 or more amino acids joined by one or more peptide bonds. Thus, the specific binding molecule may be a polypeptide. Alternatively, the specific binding molecule may comprise one or more polypeptides that comprise the CDR sequences. Preferably, the specific binding molecule for use according to the invention is an antibody or an antibody fragment.

The specific binding molecule for use according to the invention may be synthesised by any method known in the art. In particular, the specific binding molecule may be synthesised using a protein expression system, such as a cellular expression system using prokaryotic (e.g. bacterial)

cells or eukaryotic (e.g. yeast, fungus, insect or mammalian) cells. An alternative protein expression system is a cell-free, in vitro expression system, in which a nucleotide sequence encoding the specific binding molecule is transcribed into mRNA, and the mRNA translated into a protein, in vitro. Cell-free expression system kits are widely available, and can be purchased from e.g. Thermo Fisher Scientific (USA). Alternatively, specific binding molecules may be chemically synthesised in a non-biological system. Liquid-phase synthesis or solid-phase synthesis may be used to generate polypeptides that may form or be comprised within the specific binding molecule for use according to the invention. The skilled person can readily produce specific binding molecules using appropriate methodology common in the art. In particular, the specific binding molecule may be recombinantly expressed in mammalian cells, such as CHO cells.

A specific binding molecule which binds to human Anx-A1 at an epitope as defined above (i.e. consisting of amino acids 197-206, 220-224 and 227-237 of SEQ ID NO: 17) may be generated by standard methods in the art (e.g. genetic immunisation for antibodies) and an antibody with the required epitope identified by standard methods of epitope mapping known in the art. Examples of such methods include HDX, epitope excision, peptide panning, X-ray co-crystallography, NMR, etc. (Clementi et al., *Methods Mol. Biol.* 1131: 427-446, 2014; Abbott et al., Immunology 142(4): 526-535, 2014). Specific binding molecules may also be generated by modification of existing specific binding molecules known to bind the relevant epitope (e.g. by expression of modified sequences) and molecules binding the relevant epitope identified by methods described herein. Specific binding molecules binding to the relevant epitope may also be identified by competition with antibodies known to bind to the epitope (e.g. as described herein) or by comparing their binding to the epitope as disclosed herein and epitope variants thereof (in which failure to bind to an epitope variant is indicative of specific binding to the epitope of interest).

The specific binding molecule for use according to the invention may, if necessary, be isolated (i.e. purified). "Isolated", as used herein, means that the specific binding molecule is the primary component (i.e. majority component) of any solution or suchlike in which it is provided. In particular, if the specific binding molecule is initially produced in a mixture or mixed solution, isolation of the specific binding molecule means that it has been separated or purified therefrom. Thus, for instance, if the specific binding molecule is a polypeptide, and said polypeptide is produced using a protein expression system as discussed above, the specific binding molecule is isolated such that it is the most abundant polypeptide in the solution or composition in which it is present, preferably constituting the majority of polypeptides in the solution or composition, and is enriched relative to other polypeptides and biomolecules present in the native production medium. In particular, the specific binding molecule for use according to the invention is isolated such that it is the predominant (majority) specific binding molecule in the solution or composition. In a preferred feature, the specific binding molecule is present in the solution or composition at a purity of at least 60, 70, 80, 90, 95 or 99% w/w when assessed relative to the presence of other components, particularly other polypeptide components, in the solution or composition.

If the specific binding molecule is a protein, e.g. produced in a protein expression system, a solution of the specific binding molecule may be analysed by quantitative proteomics to identify whether the specific binding molecule for use according to the invention is predominant and thus isolated. For instance, 2D gel electrophoresis and/or mass spectrometry may be used. Such isolated molecules may be present in preparations or compositions as described hereinafter.

The specific binding molecule of the present invention may be isolated using any technique known in the art. For instance, the specific binding molecule may be produced with an affinity tag such as a polyhistidine tag, a strep tag, a FLAG tag, an HA tag or suchlike, to enable isolation of the molecule by affinity chromatography using an appropriate binding partner, e.g. a molecule carrying a polyhistidine tag may be purified using $Ni^{2+}$ ions. In embodiments in which the specific binding molecule is an antibody, the specific binding molecule may be isolated using affinity chromatography using one or more antibody-binding proteins, such as Protein G, Protein A, Protein A/G or Protein L. Alternatively, the specific binding molecule may be isolated by e.g. size-exclusion chromatography or ion-exchange chromatography. A specific binding molecule produced by chemical synthesis (i.e. by a non-biological method), by contrast, is likely to be produced in an isolated form. Thus, no specific purification or isolation step is required for a specific binding molecule for use according to the invention to be considered isolated, if it is synthesised in a manner that produces an isolated molecule.

In embodiments of the invention where the specific binding molecule comprises a CDR sequence which is a variant of SEQ ID NO: 1 (or 7 or 8) or 2-6, that variant may be altered relative to its reference CDR sequence (i.e. the CDR sequence to which it has at least 85%, but less than 100%, sequence identity) by substitution, addition and/or deletion of amino acid residues.

When a CDR sequence is modified by substitution of a particular amino acid residue, the substitution may be a conservative amino acid substitution. The term "conservative amino acid substitution", as used herein, refers to an amino acid substitution in which one amino acid residue is replaced with another amino acid residue having a similar side chain. Amino acids with similar side chains tend to have similar properties, and thus a conservative substitution of an amino acid important for the structure or function of a polypeptide may be expected to affect polypeptide structure/function less than a non-conservative amino acid substitution at the same position. Families of amino acid residues having similar side chains have been defined in the art, including basic side chains (e.g. lysine, arginine, histidine), acidic side chains (e.g. aspartic acid, glutamic acid), uncharged polar side chains (e.g. asparagine, glutamine, serine, threonine, tyrosine), non-polar side chains (e.g. glycine, cysteine, alanine, valine, leucine, isoleucine, proline, phenylalanine, methionine, tryptophan) and aromatic side chains (e.g. tyrosine, phenylalanine, tryptophan, histidine). Thus a conservative amino acid substitution may be considered to be a substitution in which a particular amino acid residue is substituted for a different amino acid in the same family. However, a substitution of a CDR residue may equally be a non-conservative substitution, in which one amino acid is substituted for another with a side-chain belonging to a different family.

Amino acid substitutions or additions in the scope of the invention may be made using a proteinogenic amino acid encoded by the genetic code, a proteinogenic amino acid not encoded by the genetic code, or a non-proteinogenic amino acid. Preferably any amino acid substitution or addition is made using a proteinogenic amino acid. The amino acids making up the sequence of the CDRs may include amino acids which do not occur naturally, but which are modifications of amino acids which occur naturally. Providing these non-naturally occurring amino acids do not alter the sequence and do not affect specificity, they may be used to generate CDRs described herein without reducing sequence identity, i.e. are considered to provide an amino acid of the CDR. For example derivatives of amino acids such as methylated amino acids may be used. In one embodiment the specific binding molecule for use according to the invention is not a natural molecule, i.e. is not a molecule found in nature.

Modifications to the amino acid sequences of the CDRs set out in SEQ ID NOs: 1-8 may be made using any suitable technique, such as site-directed mutagenesis of the encoding DNA sequence or solid state synthesis.

Specific binding molecules for use according to the invention may comprise the above-described CDRs. Additionally, such molecules may contain linker moieties or framework sequences to allow appropriate presentation of the CDRs. Additional sequences may also be present which may conveniently confer additional properties, e.g. peptide sequences which allow isolation or identification of the molecules containing the CDRs such as those described hereinbefore. In such cases a fusion protein may be generated.

As stated above, the specific binding molecule for use according to the invention may comprise CDRs having at least 85% sequence identity to SEQ ID NOs: 1 (or 7 or 8) and 2-6, as set out above. In another embodiment of the invention, each of the CDR sequences may be modified by the substitution, addition or deletion of up to 2 amino acids relative to SEQ ID NOs: 1 (or 7 or 8) and 2-6, with the proviso that the resultant CDR sequences have at least 85% or 90% sequence identity to SEQ ID NOs: 1 (or 7 or 8) and 2-6, as set out above. By "substitution, addition or deletion" are included combinations of substitutions, additions and deletions. Thus, in particular, VLCDR1 may have the sequence of SEQ ID NO: 1 (or 7 or 8) with 1 or 2 amino acid substitutions, additions or deletions; VLCDR2 may have the sequence of SEQ ID NO: 2 with 1 amino acid substitution, addition or deletion; VLCDR3 may have the sequence of SEQ ID NO: 3 with 1 amino acid substitution, addition or deletion; VHCDR1 may have the sequence of SEQ ID NO: 4 with 1 amino acid substitution, addition or deletion; VHCDR2 may have the sequence of SEQ ID NO: 5 with 1 or 2 amino acid substitutions, additions or deletions; and VHCDR3 may have the sequence of SEQ ID NO: 6 with 1 amino acid substitution, addition or deletion. Preferably said 1 or 2 amino acid substitutions of SEQ ID NO:1, 7 or 8 is/are at position 9 and/or 11 in that sequence.

Sequence identity may be assessed by any convenient method. However, for determining the degree of sequence identity between sequences, computer programmes that make pairwise or multiple alignments of sequences are useful, for instance EMBOSS Needle or EMBOSS stretcher (both Rice, P. et al., *Trends Genet.* 16, (6) pp. 276-277, 2000) may be used for pairwise sequence alignments while Clustal Omega (Sievers F et al., *Mol. Syst. Biol.* 7:539, 2011) or MUSCLE (Edgar, R. C., *Nucleic Acids Res.* 32(5):1792-1797, 2004) may be used for multiple sequence alignments, though any other appropriate programme may be used. Whether the alignment is pairwise or multiple, it must be performed globally (i.e. across the entirety of the reference sequence) rather than locally.

Sequence alignments and % identity calculations may be determined using for instance standard Clustal Omega parameters: matrix Gonnet, gap opening penalty 6, gap extension penalty 1. Alternatively the standard EMBOSS Needle parameters may be used: matrix BLOSUM62, gap opening penalty 10, gap extension penalty 0.5. Any other suitable parameters may alternatively be used.

For the purposes of this application, where there is dispute between sequence identity values obtained by different methods, the value obtained by global pairwise alignment using EMBOSS Needle with default parameters shall be considered valid.

As stated above, the specific binding molecule for use according to the invention is preferably an antibody or an antibody fragment. An "antibody" is an immunoglobulin having the features described hereinbefore. Also contemplated by the invention are variants of naturally occurring antibodies that retain the CDRs but are presented in a different framework, as discussed hereinafter and which function in the same way, i.e. retain specificity for the antigen. Thus antibodies include functional equivalents or homologues in which naturally occurring domains have been replaced in part or in full with natural or non-natural equivalents or homologues which function in the same way.

When the specific binding molecule for use according to the invention is an antibody, it is preferably a monoclonal antibody. By "monoclonal antibody" is meant an antibody preparation consisting of a single antibody species, i.e. all antibodies in the preparation have the same amino acid sequences, including the same CDRs, and thus bind the same epitope on their target antigen (by "target antigen" is meant the antigen containing the epitope bound by a particular antibody, i.e. the target antigen of an anti-Anx-A1 antibody is Anx-A1) with the same effect. In other words, the antibody for use according to the invention is preferably not part of a polyclonal mix of antibodies.

In an antibody, as described above, the CDR sequences are located in the variable domains of the heavy and light chains. The CDR sequences sit within a polypeptide framework, which positions the CDRs appropriately for antigen binding. Thus the remainder of the variable domains (i.e. the parts of the variable domain sequences which do not form a part of any one of the CDRs) constitute framework regions. The N-terminus of a mature variable domain forms framework region 1 (FR1); the polypeptide sequence between CDR1 and CDR2 forms FR2; the polypeptide sequence between CDR2 and CDR3 forms FR3; and the polypeptide sequence linking CDR3 to the constant domain forms FR4. In an antibody for use according to the invention the variable region framework regions may have any appropriate amino acid sequence such that the antibody binds to human Anx-A1 via its CDRs. The constant regions may be the constant regions of any mammalian (preferably human) antibody isotype.

In certain embodiments of the invention the specific binding molecule may be multi-specific, e.g. a bi-specific monoclonal antibody. A multi-specific binding molecule contains regions or domains (antigen-binding regions) that bind to at least two different molecular binding partners, e.g. bind to two or more different antigens or epitopes. In the case of a bi-specific antibody, the antibody comprises two heavy and light chains, in the formation as described above, except that the variable domains of the two heavy chains and the two light chains, respectively, are different, and thus form two different antigen-binding regions. In a multi-specific (e.g. bi-specific) binding molecule, e.g. monoclonal antibody, for use according to the invention, one of the antigen-binding regions has the CDR sequences of a specific binding molecule for use according to the invention as defined herein, and thus binds Anx-A1. The other antigen-binding region(s) of the multi-specific binding molecule for use according to the invention are different to the antigen-binding regions formed by CDRs for use according to the invention, e.g. have CDRs with sequences different to those defined herein for the specific binding molecule for use according to the invention. The additional (e.g. second) antigen-binding region(s) of the specific binding molecule, e.g. in the bi-specific antibody, may also bind Anx-A1, but at a different epitope to the first antigen-binding region which binds to Anx-A1 (which has the CDRs of the specific binding molecule for use according to the invention). Alternatively, the additional (e.g. second) antigen-binding region(s) may bind additional (e.g. a second), different antigen(s) which is(are) not Anx-A1. In an alternative embodiment, the two or more antigen-binding regions in the specific binding molecule, e.g. in an antibody, may each bind to the same antigen, i.e. provide a multivalent (e.g. bivalent) molecule.

The specific binding molecule may be an antibody fragment or synthetic construct capable of binding human Anx-A1. Thus an antibody fragment for use according to the invention comprises an antigen-binding domain (i.e. the antigen-binding domain of the antibody from which it is derived). Antibody fragments are discussed in Rodrigo et al., Antibodies, Vol. 4(3), p. 259-277, 2015. Antibody fragments for use according to the invention are preferably monoclonal (i.e. they are not part of a polyclonal mix of antibody fragments). Antibody fragments include, for example, Fab, F(ab')$_2$, Fab' and Fv fragments. Fab fragments are discussed in Roitt et al, Immunology second edition (1989), Churchill Livingstone, London. A Fab fragment consists of the antigen-binding domain of an antibody, i.e. an individual antibody may be seen to contain two Fab fragments, each consisting of a light chain and its conjoined N-terminal section of the heavy chain. Thus a Fab fragment contains an entire light chain and the $V_H$ and $C_H1$ domains of the heavy chain to which it is bound. Fab fragments may be obtained by digesting an antibody with papain.

F(ab')$_2$ fragments consist of the two Fab fragments of an antibody, plus the hinge regions of the heavy domains, including the disulphide bonds linking the two heavy chains together. In other words, a F(ab')$_2$ fragment can be seen as two covalently joined Fab fragments. F(ab')$_2$ fragments may be obtained by digesting an antibody with pepsin. Reduction of F(ab')$_2$ fragments yields two Fab' fragments, which can be seen as Fab fragments containing an additional sulfhydryl group which can be useful for conjugation of the fragment to other molecules.

Fv fragments consist of just the variable domains of the light and heavy chains. These are not covalently linked and are held together only weakly by non-covalent interactions. Fv fragments can be modified to produce a synthetic construct known as a single chain Fv (scFv) molecule. Such a modification is typically performed recombinantly, by engineering the antibody gene to produce a fusion protein in which a single polypeptide comprises both the $V_H$ and $V_L$ domains. scFv fragments generally include a peptide linker covalently joining the $V_H$ and $V_L$ regions, which contributes to the stability of the molecule. The linker may comprise from 1 to 20 amino acids, such as for example 1, 2, 3 or 4 amino acids, 5, 10 or 15 amino acids, or other intermediate numbers in the range 1 to 20 as convenient. The peptide linker may be formed from any generally convenient amino acid residues, such as glycine and/or serine. One example of a suitable linker is Gly$_4$Ser. Multimers of such linkers may be used, such as for example a dimer, a trimer, a tetramer or a pentamer, e.g. (Gly$_4$Ser)$_2$, (Gly$_4$Ser)$_3$, (Gly$_4$Ser)$_4$ or (Gly$_4$Ser)$_5$. However, it is not essential that a linker be present, and the $V_L$ domain may be linked to the $V_H$ domain by a peptide bond. An scFv is herein defined as an antibody fragment.

The specific binding molecule may be an analogue of an scFv. For example, the scFv may be linked to other specific binding molecules (for example other scFvs, Fab antibody fragments and chimeric IgG antibodies (e.g. with human frameworks)). The scFv may be linked to other scFvs so as to form a multimer that is a multi-specific binding protein, for example a dimer, a trimer or a tetramer. Bi-specific scFvs are sometimes referred to as diabodies, tri-specific scFvs as triabodies and tetra-specific scFvs as tetrabodies. In other embodiments the scFv for use according to the invention may be bound to other, identical scFv molecules, thus forming a multimer which is mono-specific but multi-valent, e.g. a bivalent dimer or a trivalent trimer may be formed.

Synthetic constructs that can be used include CDR peptides. These are synthetic peptides comprising antigen-binding determinants. Peptide mimetics can also be used. These molecules are usually conformationally-restricted organic rings that mimic the structure of a CDR loop and that include antigen-interactive side chains.

As noted above, in particular embodiments the specific binding molecule for use according to the present invention comprises CDRs having the amino acid sequences set forth in SEQ ID NO: 1, 7 or 8 and 2-6. As detailed, these are derived or modified from the murine antibody Mdx001. However, an antibody or fragment thereof for use according to the present invention is preferably human or humanised.

The antibody or antibody fragment for use according to the invention may be a human/mouse chimeric antibody, or preferably may be humanised. This is particularly the case for monoclonal antibodies and antibody fragments. Humanised or chimeric antibodies or antibody fragments are desirable when the molecule is to be used as a human therapeutic. Therapeutic treatment of humans with non-human (e.g. murine) antibodies can be ineffective for a number of reasons, e.g. a short in vivo half-life of the antibody; weak effector functions mediated by the foreign heavy chain constant region, due to low recognition of non-human heavy chain constant regions by Fc receptors on human immune effector cells; patient sensitisation to the antibody, and (in the context of murine antibodies) generation of a human anti-mouse antibody (HAMA) response; and neutralisation of the mouse antibody by HAMA leading to loss of therapeutic efficacy.

A chimeric antibody is an antibody with variable regions derived from one species and constant regions derived from another. Thus an antibody or antibody fragment for use according to the invention may be a chimeric antibody or chimeric antibody fragment, comprising murine variable domains and human constant domains.

As detailed above, the isotype of an antibody is defined by the sequence of its heavy chain constant regions. The chimeric antibody for use according to the invention may have the constant regions of any human antibody isotype, and any sub-class within each isotype. For instance, the chimeric antibody may have the Fc regions of an IgA, IgD, IgE, IgG or IgM antibody (i.e. the chimeric antibody may comprise the constant domains of heavy chains α, δ, ε, γ, or μ, respectively), though preferably the antibody for use according to the invention is of the IgG isotype. Thus the chimeric antibody may be of any isotype. The light chain of the chimeric antibody may be either a κ or λ light chain, i.e. it may comprise the constant region of a human λ light chain or a human κ light chain. A chimeric antibody fragment is, correspondingly, an antibody fragment comprising constant domains (e.g. an Fab, Fab' or F(ab')$_2$ fragment). The constant domains of a chimeric antibody fragment for use according to the invention may be as described above for a chimeric monoclonal antibody.

Chimeric antibodies may be generated using any suitable technique, e.g. recombinant DNA technology in which the DNA sequence of the murine variable domain is fused to the DNA sequence of the human constant domain(s) so as to encode a chimeric antibody. A chimeric antibody fragment may be obtained either by using recombinant DNA technology to produce a DNA sequence encoding such a polypeptide, or by processing a chimeric antibody for use according to the invention to produce the desired fragments, as described above. Chimeric antibodies can be expected to overcome the problems of a short in vivo half-life and weak effector functions associated with using a foreign, e.g. murine, antibody in human therapy, and may reduce the probability of patient sensitisation and HAMA occurring. However, patient sensitisation and HAMA may still occur when a chimeric antibody is administered to a human patient, due to the presence of murine sequences in the variable domains.

Preferably the antibody or antibody fragment for use according to the invention is therefore fully humanised. A humanised antibody is an antibody derived from another species, e.g. a mouse, in which the constant domains of the antibody chains are replaced with human constant domains, and the amino acid sequences of the variable regions are modified to replace the foreign (e.g. murine) framework sequences with human framework sequences, such that, preferably, the only non-human sequences in the antibody are the CDR sequences. A humanised antibody can overcome all the problems associated with therapeutic use of a non-human antibody in a human, including avoiding or minimising the probability of patient sensitisation and HAMA occurring.

Antibody humanisation is generally performed by a process known as CDR grafting, though any other technique in the art may be used. Antibody grafting is well described in Williams, D. G. et al., Antibody Engineering Vol. 1, edited by R. Kontermann and S. Dubel, Chapter 21, pp. 319-339. In this process, a chimeric antibody as described above is first generated. Thus in the context of humanisation of an antibody, the non-human constant domain is first replaced with a human constant domain, yielding a chimeric antibody comprising a human constant domain and non-human variable domain.

Subsequent humanisation of the foreign, e.g. murine, variable domains involves intercalating the murine CDRs from each immunoglobulin chain within the FRs of the most appropriate human variable region. This is done by aligning the murine variable domains with databases of known human variable domains (e.g. IMGT or Kabat). Appropriate human framework regions are identified from the best-aligned variable domains, e.g. domains with high sequence identity between the human and murine framework regions, domains containing CDRs of the same length, domains having the most similar structures (based on homology modelling), etc. The murine CDR sequences are then grafted into the lead human framework sequences at the appropriate locations using recombinant DNA technology, and the humanised antibodies then produced and tested for binding to the target antigen. The process of antibody humanisation is known and understood by the skilled individual, who can perform the technique without further instruction. Antibody humanisation services are also offered by a number of commercial companies, e.g. GenScript (USA/China) or MRC Technology (UK). Humanised antibody fragments can be easily obtained from humanised antibodies, as described above.

Alternatively, fully human monoclonal antibodies can be obtained in vitro and without immunisation using phage display technology, as described in Frenzel et al. (*Transfus. Med. Hemother.* 44(5): 312-318, 2017).

Thus the antibody or antibody fragment for use according to the invention may be derived from any species, e.g. it may be a murine antibody or antibody fragment. It is preferred, however, that the antibody or antibody fragment is a chimeric antibody or antibody fragment, i.e. that only the variable domains of the antibody or antibody fragment are non-human, and the constant domains are all human. Optimally, the antibody or antibody fragment for use according to the invention is a human or humanised antibody or antibody fragment.

Humanised versions of Mdx001 have been developed by the inventors, as detailed in WO 2018/146230. Humanised light chain variable domains have been developed with the amino acid sequences set forth in SEQ ID NO: 9 (known as the L1M2 variable region) and SEQ ID NO: 10 (known as the L2M2 variable region), containing the CDRs as described hereinbefore. In a particular embodiment, the antibody or fragment thereof for use according to the invention comprises a light chain variable region comprising or consisting of the amino acid sequence set forth in SEQ ID NO: 9 or SEQ ID NO: 10, or an amino acid sequence having at least 70% (preferably at least 80, 90, 95, 96, 97, 98 or 99%) sequence identity thereto, and in which the CDR sequences VLCDR1-3 have at least 85% sequence identity to SEQ ID NOs: 1, 7 or 8 and 2-3 respectively.

Humanised heavy chain variable domains have been developed with the amino acid sequences set forth in SEQ ID NO: 11 (known as the H4 variable region) and SEQ ID NO: 12 (known as the H2 variable region). In a particular embodiment, the antibody or fragment thereof for use according to the invention comprises a heavy chain variable region comprising or consisting of the amino acid sequence set forth in SEQ ID NO: 11 or SEQ ID NO: 12, or an amino acid sequence having at least 70% (preferably at least 80, 90, 95, 96, 97, 98 or 99%) sequence identity thereto, and in which the CDR sequences VHCDR1-3 have at least 85% sequence identity to SEQ ID NOs: 4-6 respectively.

In a particular embodiment, the specific binding molecule for use according to the invention is a monoclonal antibody of the IgG1 isotype and comprises light chains of the K subtype. The L1M2 light chain is of the K subtype and has the amino acid sequence set forth in SEQ ID NO: 13. The H4 heavy chain has the amino acid sequence set forth in SEQ ID NO: 14. In a particular embodiment, the specific binding molecule for use according to the invention is the L1M2H4 antibody that comprises the L1M2 light chain and the H4 heavy chain. Thus the specific binding molecule for use according to the invention may be a monoclonal antibody comprising or consisting of:

i) a light chain comprising or consisting of the amino acid sequence set forth in SEQ ID NO: 13, or an amino acid sequence having at least 70% (preferably at least 80, 90, 95, 96, 97, 98 or 99%) sequence identity thereto, and in which the CDR sequences VLCDR1-3 have at least 85% sequence identity to SEQ ID NOs: 1, 7 or 8 and 2-3 respectively; and ii) a heavy chain comprising or consisting of the amino acid sequence set forth in SEQ ID NO: 14, or an amino acid sequence having at least 70% (preferably at least 80, 90, 95, 96, 97, 98 or 99%) sequence identity thereto, and in which the CDR sequences VHCDR1-3 have at least 85% sequence identity to SEQ ID NOs: 4-6 respectively.

Similarly, the L2M2 light chain is of the K subtype and has the amino acid sequence set forth in SEQ ID NO: 15. The H2 heavy chain has the amino acid sequence set forth in SEQ ID NO: 16. In a particular embodiment, the specific binding molecule for use according to the invention is the L2M2H2 antibody that comprises the L2M2 light chain and the H2 heavy chain. Thus the specific binding molecule for use according to the invention may be a monoclonal antibody comprising:
  i) a light chain comprising or consisting of the amino acid sequence set forth in SEQ ID NO: 15, or an amino acid sequence having at least 70% (preferably at least 80, 90, 95, 96, 97, 98 or 99%) sequence identity thereto, and in which the CDR sequences VLCDR1-3 have at least 85% sequence identity to SEQ ID NOs: 1, 7 or 8 and 2-3 respectively; and
  ii) a heavy chain comprising or consisting of the amino acid sequence set forth in SEQ ID NO: 16, or an amino acid sequence having at least 70% (preferably at least 80, 90, 95, 96, 97, 98 or 99%) sequence identity thereto, and in which the CDR sequences VHCDR1-3 have at least 85% sequence identity to SEQ ID NOs: 4-6 respectively.

In an alternative embodiment, the L1M2 light chain may be paired with the H2 heavy chain and the L2M2 light chain may be paired with the H4 heavy chain.

As is known to the skilled person, antibody chains are produced in nature with signal sequences. Antibody signal sequences are amino acid sequences located at the N-termini of the light and heavy chains, N-terminal to the variable regions. The signal sequences direct the antibody chains for export from the cell in which they are produced. If produced in a cellular expression system, the light and heavy chains with the amino acid sequences of SEQ ID NOs: 13-16 may be encoded with a signal sequence. The signal sequence of the L1M2 and L2M2 light chains is set forth in SEQ ID NO: 20; the signal sequence of the H2 and H4 heavy chains is set forth in SEQ ID NO: 21. If synthesised with a signal sequence, the L1M2 chain may thus be synthesised with the amino acid sequence set forth in SEQ ID NO: 22; the H4 chain may be synthesised with the amino acid sequence set forth in SEQ ID NO: 23; the L2M2 chain may be synthesised with the amino acid sequence set forth in SEQ ID NO: 24 and the H2 chain may be synthesised with the amino acid sequence set forth in SEQ ID NO: 25. Nucleotide sequences encoding such sequences may be easily derived by the skilled person, but examples of suitable nucleotide sequences which encode the antibody chains of SEQ ID NOs: 22-25, and may be used for their synthesis, are set forth in SEQ ID NOs: 26-29, respectively.

As detailed above, the invention provides a specific binding molecule (as described above) for use in the treatment of cancer in a subject. Use in the treatment of any cancer is covered, including the treatment of testicular cancer, ovarian cancer, colorectal cancer, cervical cancer, breast cancer, bladder cancer, bile duct cancer, stomach cancer, head and neck cancers, oesophageal cancer, lung cancer, pancreatic cancer, mesothelioma, lymphoma, brain tumours and neuroblastoma. In a preferred aspect ovarian cancer is treated. In another preferred aspect, breast cancer is treated. In a preferred embodiment, the breast cancer expresses one or more of an oestrogen receptor (ER), a progesterone receptor (PR) and the human epidermal growth factor receptor HER2. In another embodiment, the breast cancer is triple negative (i.e. ER-/PR-/HER2-). In another preferred aspect colorectal cancer is treated. In another preferred aspect pancreatic cancer is treated. In another preferred aspect lung cancer is treated. Any type of cancer may be treated according to the present invention, including carcinoma (including adenocarcinoma, squamous cell carcinoma, basal cell carcinoma, transitional cell carcinoma, etc.), sarcoma, leukaemia and lymphoma.

According to the invention, cancer of any stage (or grade) may be treated, including stage I, stage II, stage III and stage IV cancer. Both metastatic and localised (i.e. non-metastatic) cancer may be treated.

In a particular embodiment of the invention the cancer expresses Anx-A1 (by which is meant that the cells in the cancer express Anx-A1, e.g. on the cells' surface). It is straightforward for the skilled person to determine whether a cancer expresses Anx-A1. Anx-A1 expression may be analysed in a biopsy sample of a cancer, e.g. at the protein level by immunohistochemistry analysis of a sample. A sample may be immunostained using an anti-Anx-A1 antibody (such as the antibodies described above which may be used according to the invention) to detect Anx-A1 expression, following standard procedures in the art. By permeabilizing a sample (e.g. using a detergent, as is standard in the art) both intracellular and extracellular Anx-A1 may be detected.

Alternatively, Anx-A1 expression may be analysed at the nucleic acid level, e.g. by quantitative PCR (qPCR). mRNA may be extracted from a tissue sample and reverse transcribed into DNA using procedures standard in the art. Anx-A1 expression levels may then be determined by quantitative amplification of a target Anx-A1 sequence. Suitable qPCR techniques, e.g. TaqMan, are well known in the art.

In a particular embodiment, the cancer overexpresses Anx-A1. By "overexpresses Anx-A1" is meant that the cancer expresses Anx-A1 at a higher level than healthy tissue from the same source. That is to say, the cancerous cells express Anx-A1 at a higher level than do healthy (i.e. non-cancerous) cells from the same source. By the same source is meant the same tissue. For instance, an ovarian epithelial cell carcinoma may be considered to overexpress Anx-A1 if it expresses Anx-A1 at a higher level than does healthy ovarian epithelial tissue. Whether a cancer tissue overexpresses Anx-A1 thus requires quantitative comparison of Anx-A1 expression in at least two different tissues (the cancer tissue and a healthy control tissue). Any appropriate technique may be utilised to perform this comparison, though qPCR may be most suitable. It would be straightforward for the skilled person to determine whether a cancer overexpresses Anx-A1. In a particular embodiment, the difference between the level of Anx-A1 expression in the cancer that overexpresses it and healthy tissue is statistically significant. In other embodiments, Anx-A1 expression is increased by at least 10, 20, 30, 40, 50, 60, 70, 80, 90 or 100% or more in the cancerous tissue relative to corresponding healthy tissue.

In another embodiment of the invention, the cancer expresses Anx-A1 on its surface (that is to say, Anx-A1 is expressed on the surface of the cells of the cancer). By expression of Anx-A1 on the surface of cancer cells is meant that the cells express Anx-A1, and the expressed Anx-A1 is exported and localised on the cell surface. Cell surface expression of Anx-A1 may be identified by immunohistochemistry, as described above. In particular, to analyse cell surface expression of Anx-A1, the immunohistochemistry analysis is performed without cell permeabilization. This means that the antibody used to detect Anx-A1 on the tissue is unable to enter the interior of the cells and only extracellular (e.g. surface-located) protein may be detected. Exported Anx-A1 generally attaches to cell surfaces (rather than being released into plasma or any other extracellular space), and thus any Anx-A1 detected by immunohistochemistry of non-permeabilized cells may be considered to be surface-located Anx-A1. Nonetheless, following standard protocols, tissue may be washed prior to staining to remove loose extracellular material, including proteins.

The cancer treated by the present invention may be a drug-resistant cancer. That is to say the cancer may be resistant to one or more chemotherapeutic agents (chemotherapy drugs). Drug resistance in cancer is reviewed in Housman et al. (supra). A cancer may be considered resistant to a chemotherapy drug if it is able to tolerate it, i.e. if the drug is (or becomes) ineffective against the cancer. As detailed in Housman et al. (supra), cancers may become drug-resistant by a variety of different mechanisms, including inactivation or metabolism of drugs (or the prevention of their metabolic activation), mutation or alteration of the drug target and drug efflux via ABC transporters. Methods for identifying whether a cancer is drug-resistant are known in the art, see for instance the teachings of Wang et al. (Genes & Diseases 2: 219-221, 2015) and Volm & Efferth (*Front. Oncol.* 5: 282, 2015), both incorporated herein by reference. Such methods include testing the effect of a drug on a cell population ex vivo and genetic screening of cancer cells for susceptibility/resistance markers.

In a particular embodiment, the cancer treated by the present invention is multidrug resistant (MDR). By MDR cancer is meant a cancer that is resistant to more than one chemotherapy drug, in particular more than one family of chemotherapy drug. MDR cancer may be resistant to 2, 3, 4 or 5 or more different chemotherapy drugs, or chemotherapy drug families (or classes). The term "MDR cancer" is well known in the art and is used in the present context in accordance with its meaning in the art. MDR cancer may be resistant to all known chemotherapy drugs. Multidrug resistance may be mediated by expression of one or more of the ABC transporters multidrug resistance protein 1 (MDR1), multidrug resistance-associated protein 1 (MRP1) and breast cancer resistance protein (BCRP). All three have broad substrate specificity and are able to expel chemotherapy agents of multiple different classes from cells that express them.

Specific binding molecules for use according to the present invention are shown in the Examples to be particularly effective in inhibiting the proliferation of cancer cells which are resistant to platinum-based chemotherapy. In a particular embodiment, the cancer treated according to the present invention is resistant to platinum-based chemotherapeutic agents. (Preferably the cancer in this case is a breast cancer, colorectal cancer, ovarian cancer, lung cancer or pancreatic cancer.) Platinum-based chemotherapy agents include cisplatin, oxaliplatin, carboplatin and nedaplatin, all of which have been approved for use in humans. Other known platinum-based chemotherapeutic agents include satraplatin, picoplatin, phenanthriplatin and triplatin tetranitrate. The cancer treated according to the present invention may be resistant to any or all of these agents. In a particular embodiment, the cancer is resistant to cisplatin.

The cancer cells may also or alternatively be resistant to other bi-functional alkylating agents including nitrogen mustards (e.g. bendamustine, chlorambucil, cyclophosphamide, ifosfamide, mechlorethamine and melphalan).

In an alternative or additional embodiment, the cancer treated according to the present invention may be resistant to chemotherapeutic agents such as taxanes (such as paclitaxel and docetaxel), topoisomerase inhibitors (such as topotecan), anthracyclines (such as doxorubicin and epirubicin) and nucleoside analogues (such as gemcitabine). Preferably the chemotherapeutic agent in this embodiment is an anthracycline, e.g. doxorubicin (also known as adriamycin). In another embodiment the cancer treated according to the present invention is resistant to hormone therapeutics (e.g. anti-oestrogen hormonal therapeutics, such as tamoxifen). Breast cancer may in particular be resistant to hormone therapeutics such as tamoxifen. The cancer treated according to the present invention may be resistant to any or all of these agents. (Preferably the cancer in this case is a breast cancer, colorectal cancer, ovarian cancer, lung cancer or pancreatic cancer.) In a particular embodiment, the cancer is resistant to doxorubicin (optionally in addition to resistance to a platinum-based chemotherapeutic agent).

Cancer cells may acquire resistance to platinum-based chemotherapy agent by a number of mechanisms, as discussed above. For instance, production of metallothioneins and/or glutathione by the cancer can lead to inactivation of platinum-based agents, while DNA damage induced by such agents can be repaired by active pathways of nucleotide excision repair and homologous recombination, thus reversing the action of the platinum-based agent. Other mechanisms may also play a role, and multiple non-redundant mechanisms may be required to render a cell resistant to platinum-based therapy. Patients identified as platinum-resistant exhibit tumour progression within 6 months of their last platinum-based chemotherapy treatment. Cells may be identified as platinum resistant by use of the clonogenic assay to test reproductive cell survival after drug exposure. This identifies if cancer cells are able to form tumours or colonies after drug exposure.

The specific binding molecule may be administered to the subject to be treated in the form of a pharmaceutical composition. Such a composition may contain one or more pharmaceutically acceptable diluents, carriers or excipients. "Pharmaceutically acceptable" as used herein refers to ingredients that are compatible with other ingredients of the compositions as well as physiologically acceptable to the recipient. The nature of the composition and carriers or excipient materials, dosages etc. may be selected in routine manner according to choice and the desired route of administration, etc. Dosages may likewise be determined in routine manner and may depend upon the nature of the molecule, age of patient, mode of administration etc.

The pharmaceutical composition may be prepared for administration to a subject by any suitable means. Such administration may be e.g. oral, rectal, nasal, topical, vaginal or parenteral. Oral administration as used herein includes buccal and sublingual administration. Topical administration as used herein includes transdermal administration. Parenteral administration as defined herein includes subcutaneous, intramuscular, intravenous, intraperitoneal and intradermal administration.

Pharmaceutical compositions as disclosed herein include liquid solutions or syrups, solid compositions such as powders, granules, tablets or capsules, creams, ointments and any other style of composition commonly used in the art. Suitable pharmaceutically acceptable diluents, carriers and excipients for use in such compositions are well known in the art. For instance, suitable excipients include lactose, maize starch or derivatives thereof, stearic acid or salts thereof, vegetable oils, waxes, fats and polyols. Suitable carriers or diluents include carboxymethylcellulose (CMC), methylcellulose, hydroxypropylmethylcellulose (HPMC), dextrose, trehalose, liposomes, polyvinyl alcohol, pharmaceutical grade starch, mannitol, lactose, magnesium stearate, sodium saccharin, talcum, cellulose, glucose, sucrose (and other sugars), magnesium carbonate, gelatin, oil, alcohol, detergents and emulsifiers such as the polysorbates. Stabilising agents, wetting agents, emulsifiers, sweeteners etc. may also be used.

Liquid pharmaceutical compositions, whether they be solutions, suspensions or other like form, may include one or more of the following: sterile diluents such as water for injection, Ringer's solution, isotonic sodium chloride, fixed oils such as synthetic mono- or diglycerides which may serve as a solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as EDTA; buffers such as acetates, citrates or phosphates and agents for the adjustment of tonicity such as dextrose. A parenteral preparation can be enclosed in ampoules, disposable syringes or multiple dose vials made of glass or plastic. An injectable pharmaceutical composition is preferably sterile.

Pharmaceutical compositions for use according to the present invention may be administered in any appropriate manner. The quantity and frequency of administration will be determined by such factors as the condition of the patient, and the type and severity of the patient's disease, although appropriate dosages may be determined by clinical trials. Conveniently a specific binding molecule for use according to the invention may be provided to a subject in a daily, weekly or monthly dose, or a dose in an intermediate frequency, e.g. a dose may be provided every 2, 3, 4, 5 or 6 days, every 2, 3, 4, 5 or 6 weeks, every 2, 3, 4, 5 or 6 months, annually or biannually. The dose may be provided in the amount of from 10 ng/kg to 100 mg/kg, e.g. 1 µg/kg to 10 mg/kg body weight, for example from 10 µg/kg to 1 mg/kg. The skilled clinician will be able to calculate an appropriate dose for a patient based on all relevant factors, e.g. age, height, weight, and condition to be treated.

Preferably, the specific binding molecule or pharmaceutical composition for use according to the invention is administered to the subject in need thereof in a therapeutically effective amount. By "therapeutically effective amount" is meant an amount sufficient to show benefit to the condition of the subject. Whether an amount is sufficient to show benefit to the condition of the subject may be determined by the physician/veterinarian.

The treatment may further comprise the administration of a second therapeutic agent to the subject. Conveniently however, in uses according to the invention the specific binding molecule is the sole therapeutic molecule used in the treatment, for example the treatment is not carried out in conjunction with other cytotoxic or immunotherapeutic agents. Cytotoxic agents are as described hereinafter. Immunotherapeutic agents are administered agents that act to induce, enhance or suppress an immune response.

In a particular embodiment, the specific binding molecule for use according to the present invention is not used to deliver a second therapeutic molecule to a target cancer. For instance, in a particular embodiment the specific binding molecule is not conjugated to (and does not provide a binding partner for) a second therapeutic molecule, such as a cytotoxic molecule or a radionuclide.

When used, the second therapeutic agent may be administered within the same pharmaceutical composition as the specific binding molecule which binds Anx-A1, or within a separate pharmaceutical composition, which may be as described above. (Thus, in uses in which a medicament is made, the medicament may contain the specific binding molecule (or a second therapeutic agent) and said treatment may comprise separate, sequential or simultaneous administration of the second therapeutic agent (or specific binding molecule) with the medicament.) The specific binding molecule which binds Anx-A1 and the second therapeutic agent may be administered to the subject separately, simultaneously or sequentially. "Separate" administration, as used herein, means that the specific binding molecule and the second therapeutic agent are administered to the subject at the same time, or at least substantially the same time, but by different administrative routes. "Simultaneous" administration, as used herein, means that the specific binding molecule and the second therapeutic agent are administered to the subject at the same time, or at least substantially the same time, by the same administrative route. By "sequential" administration, as used herein, is meant that the specific binding molecule and the second therapeutic agent are administered to the subject at different times. In particular, administration of the first therapeutic agent is completed before administration of the second therapeutic agent commences. Sequential administration may be performed in which the first and second therapeutic agents are administered from 10 minutes to 30 days apart, e.g. from 1 hour to 96 hours (or 2 weeks) apart. When administered to a subject sequentially, the first and second therapeutic agents may be administered by the same administrative route or by different administrative routes.

The second therapeutic agent may be a second anti-cancer agent, though in other embodiments may have a different activity, e.g. it may be an anti-bacterial or anti-fungal agent, or any other agent useful for in the treatment of the patient. In a particular embodiment, the second therapeutic agent is a chemotherapeutic agent, in particular a cytotoxic agent. As referred to herein a chemotherapeutic agent is an administered drug which is destructive to malignant cells and tissues. A cytotoxic agent is a substance that destroys cells or prevents their multiplication. Any chemotherapy agent of any class may be used, e.g. taxanes (such as paclitaxel and docetaxel), topoisomerase inhibitors (such as topotecan), anthracyclines (such as doxorubicin and epirubicin), nucleoside analogues (such as gemcitabine), platinum-based agents (such as cisplatin and carboplatin), alkylating agents (such as cyclophosphamide) and kinase inhibitors (such as imatinib) or other chemotherapeutic agents or drugs as described hereinbefore.

Such agents may be used in combination with the specific binding molecule for use according to the invention. In one aspect the chemotherapeutic agent may be an agent to which the cancer is resistant (when treated without the specific binding molecule for use in the invention). In the alternative, the chemotherapeutic agent is not an agent to which the cancer is resistant (when treated without the specific binding molecule for use in the invention).

The specific binding molecule for use according to the invention may also be administered to the subject in combination with radiotherapy and/or surgery.

As detailed above, the present invention is directed to the treatment of cancer in a subject. Treatment may be (or may be intended to be) curative, but may alternatively be palliative (i.e. designed merely to limit, relieve or improve the symptoms of the cancer, or to extend survival). Preferably the size of the tumour is reduced by the treatment or its rate of growth is stabilized or decreased. A reduction of at least 10%, preferably at least 20, 30 or 50% (e.g. up to 30, 50, 75 or 100%) in tumour size is preferred and the same levels of growth decrease are preferred.

The subject treated by the invention may be any mammal, e.g. a farm animal such as a cow, horse, sheep, pig or goat, a pet animal such as a rabbit, cat or dog, or a primate such as a monkey, chimpanzee, gorilla or human. Most preferably the subject is a human. The subject may be any animal (preferably human) who is suffering from cancer, or is suspected to be suffering from cancer. Thus the subject is an individual in need of treatment for cancer.

The present invention may thus be seen as providing a method of treating cancer in a subject, comprising administering to said subject a specific binding molecule which binds human Anx-A1. The treatment, cancer, subject and/or specific binding molecule may be as defined above.

Similarly, the present invention can be seen to provide the use of a specific binding molecule which binds human Anx-A1 in the manufacture of a medicament for the treatment of cancer in a subject. The treatment, cancer, subject and/or specific binding molecule may be as defined above.

In another aspect, the invention provides a kit comprising a specific binding molecule which binds human Anx-A1, as defined above, and a chemotherapeutic agent. Suitable chemotherapeutic agents are described above. The specific binding molecule and chemotherapeutic agent may be provided in separate containers, i.e. in separate compositions, or in a single composition in a single container. Each therapeutic agent may be provided in any appropriate form, e.g. in an aqueous solution or as a lyophilisate.

In another aspect, the invention provides a product comprising a specific binding molecule which binds human Anx-A1, as defined above, and a second therapeutic agent for separate, simultaneous or sequential use in the treatment of cancer in a subject. The second therapeutic agent, cancer and/or subject may be as defined above. In a particular embodiment, the second therapeutic agent is a chemotherapeutic agent. The specific binding molecule and second therapeutic agent may be provided in separate containers, i.e. in separate compositions, or in a single composition in a single container. Each therapeutic agent may be provided in any appropriate form, e.g. in an aqueous solution or as a lyophilisate.

All documents cited in the present application are hereby wholly incorporated herein by reference.

The invention may be further understood by reference to the figures and non-limiting examples below.

Figure 8:
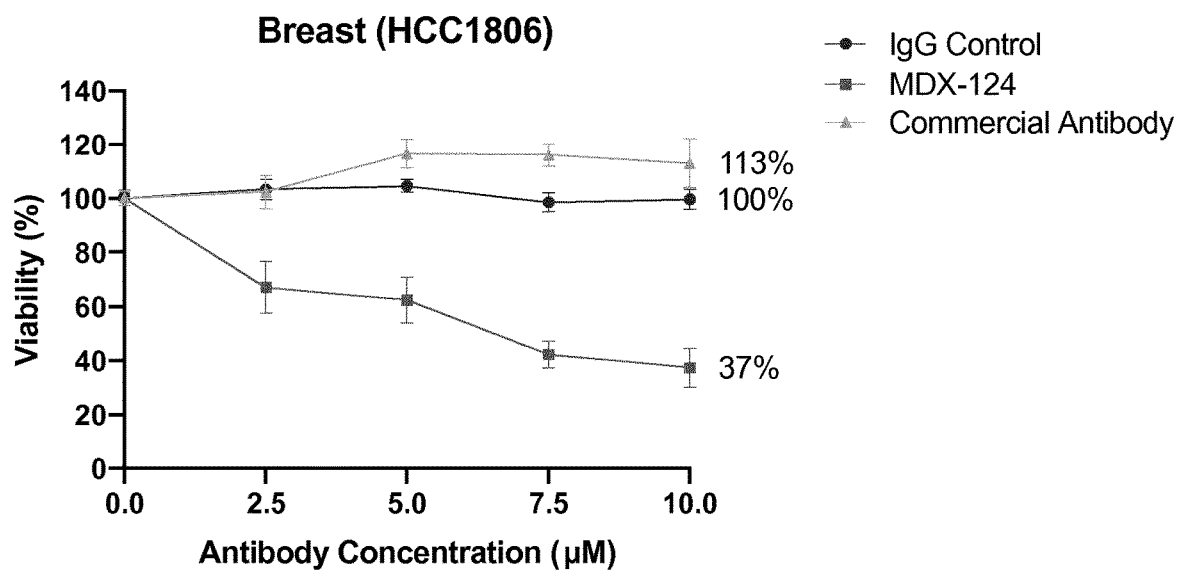

FIG. 8 shows the effect of the anti-Anx-A1 antibodies MDX-124 and ab65844 on the proliferation of the breast cancer cell line HCC1806. The impact of a non-specific control IgG is also shown. Error bars indicate standard error of the mean.

Figure 9:
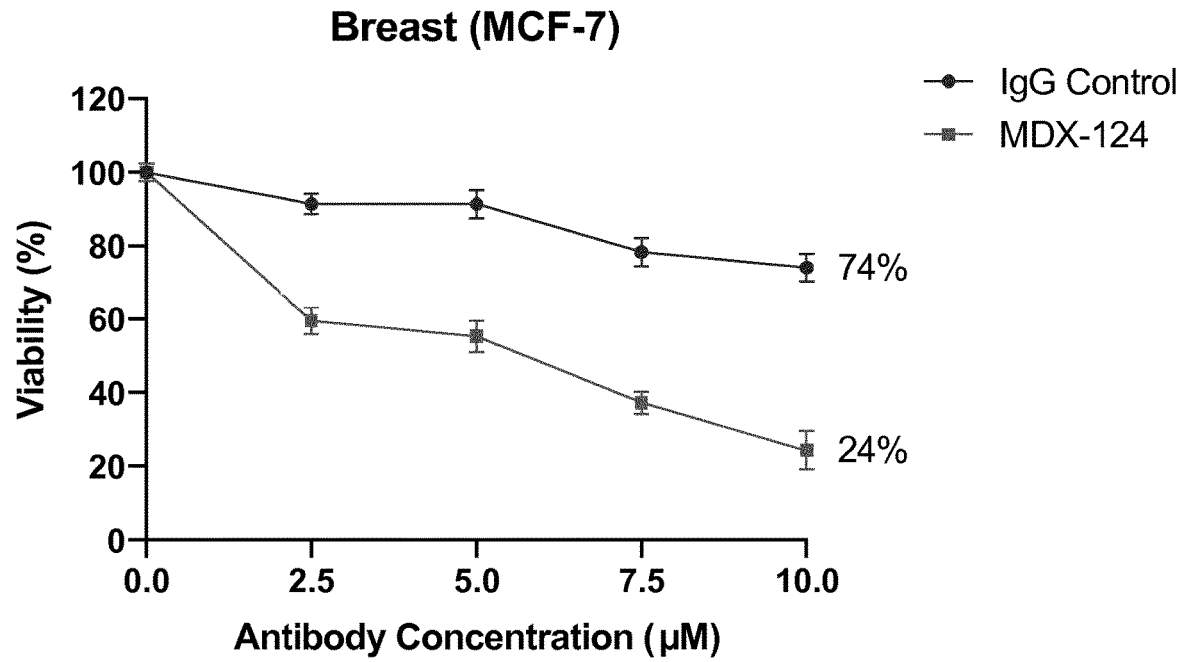

FIG. 9 shows the effect of the anti-Anx-A1 antibody MDX-124 and a non-specific control IgG on the proliferation of the breast cancer cell line MCF7. Error bars indicate standard error of the mean.

Figure 10:
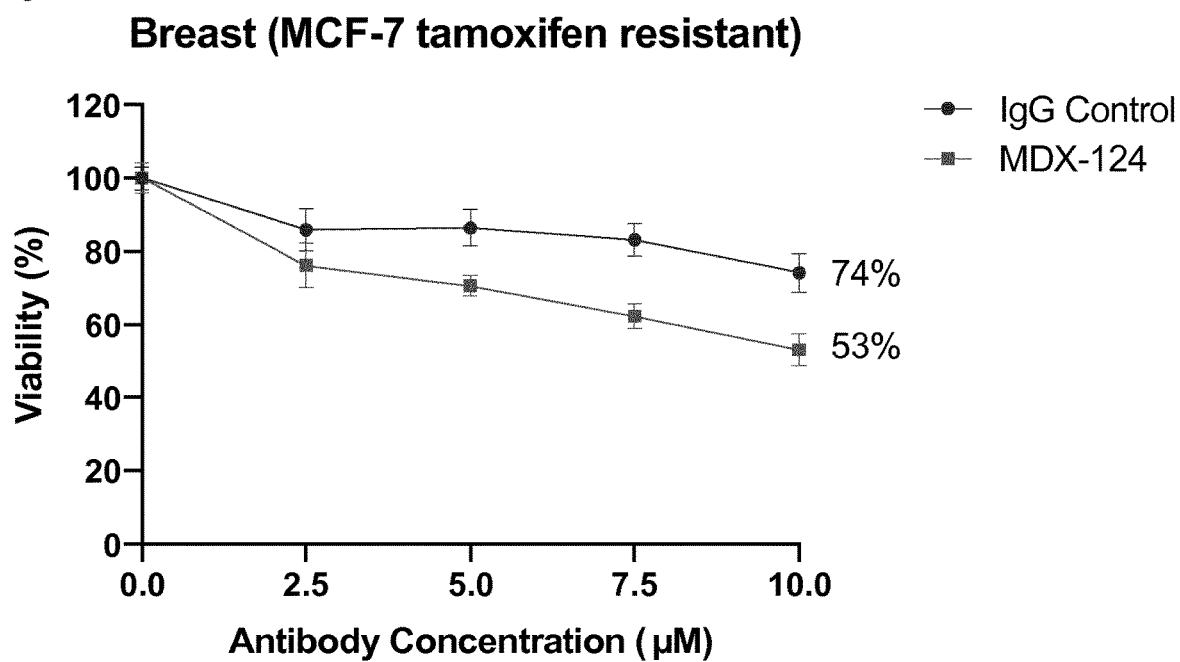

FIG. 10 shows the effect of the anti-Anx-A1 antibody MDX-124 and a non-specific control IgG on the proliferation of the tamoxifen-resistant breast cancer cell line MCF-7/TAMR7. Error bars indicate standard error of the mean.

Figure 11:
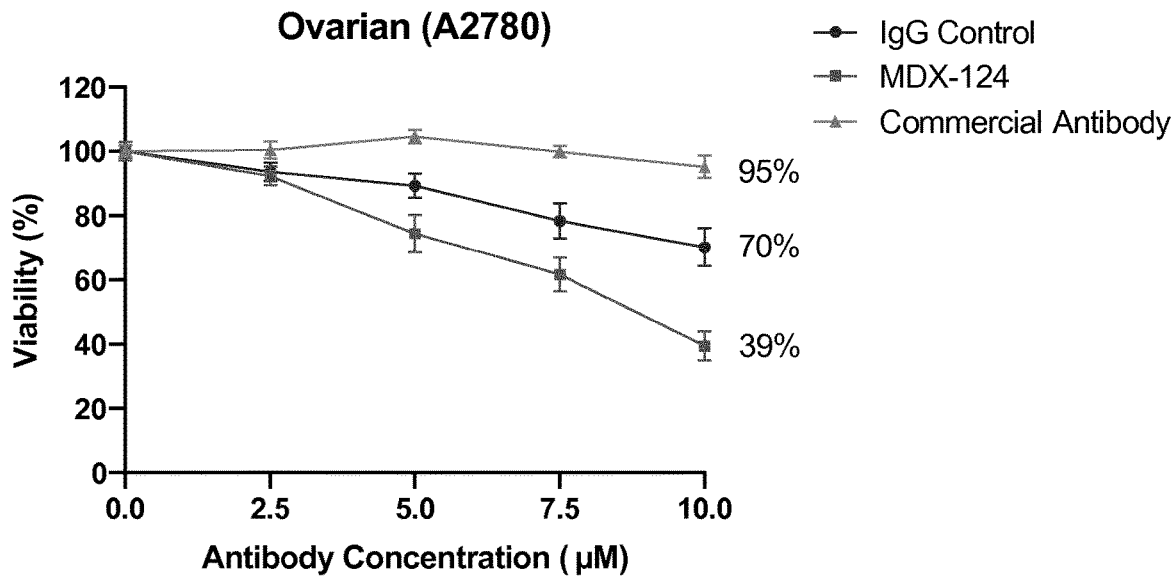

FIG. 11 shows the effect of the anti-Anx-A1 antibodies MDX-124 and ab65844 on the proliferation of the ovarian cancer cell line A2780. The impact of a non-specific control IgG is also shown. Error bars indicate standard error of the mean.

Figure 12:
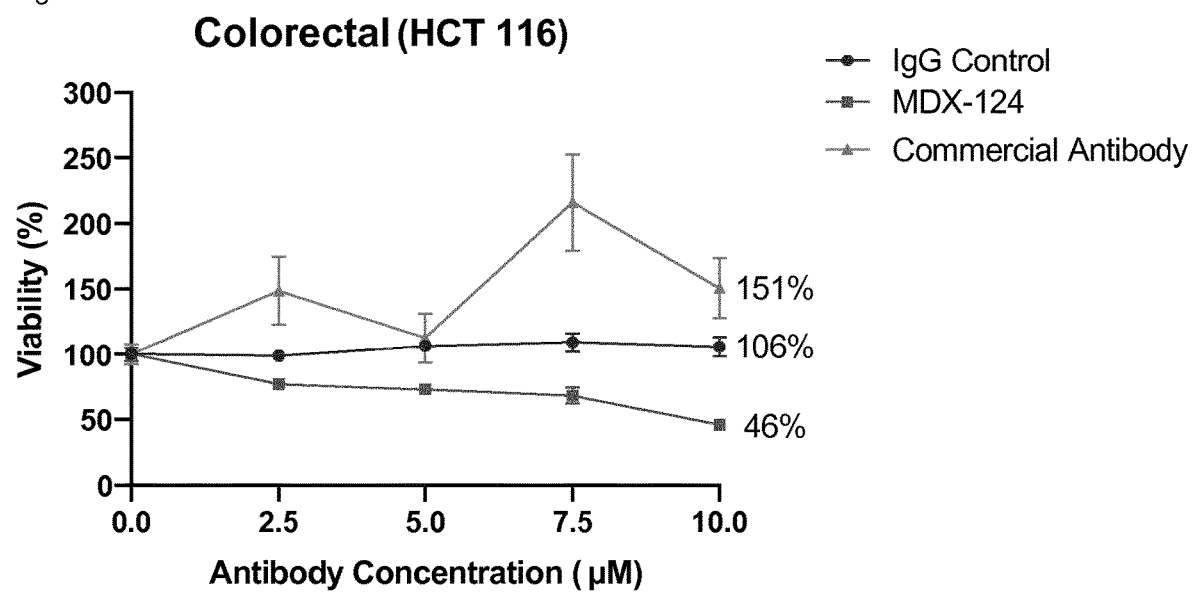

FIG. 12 shows the effect of the anti-Anx-A1 antibodies MDX-124 and ab65844 on the proliferation of the colorectal cancer cell line HCT116. The impact of a non-specific control IgG is also shown. Error bars indicate standard error of the mean.

Figure 13:
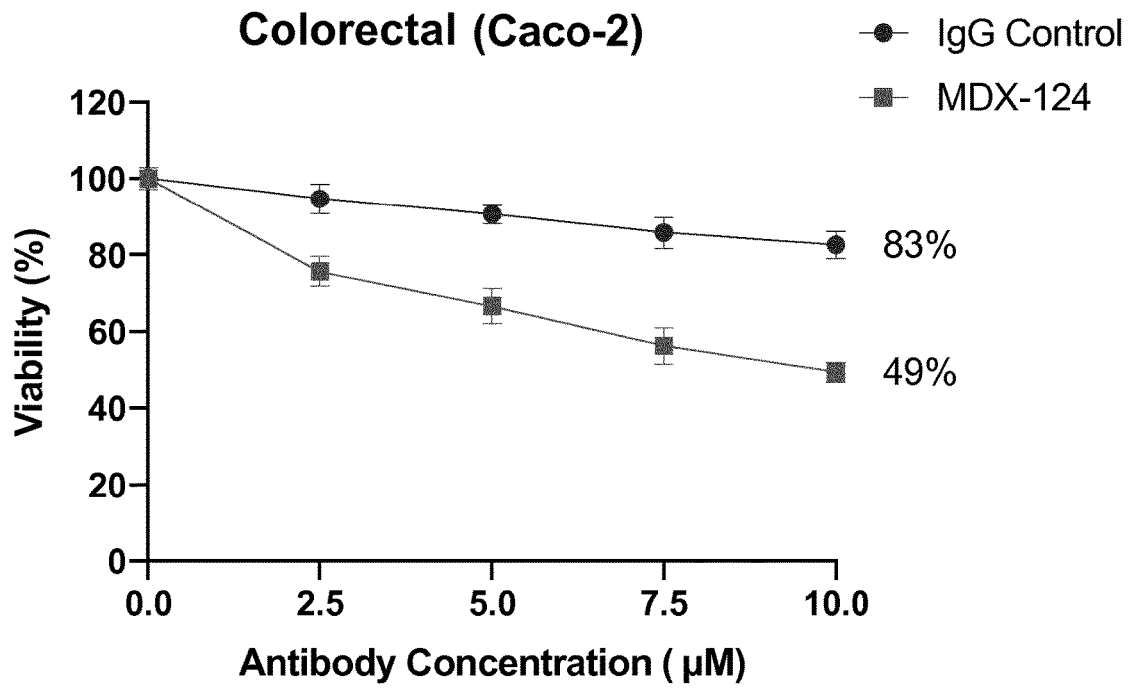

FIG. 13 shows the effect of the anti-Anx-A1 antibody MDX-124 and a non-specific control IgG on the proliferation of the colorectal cancer cell line Caco-2. Error bars indicate standard error of the mean.

Figure 14:
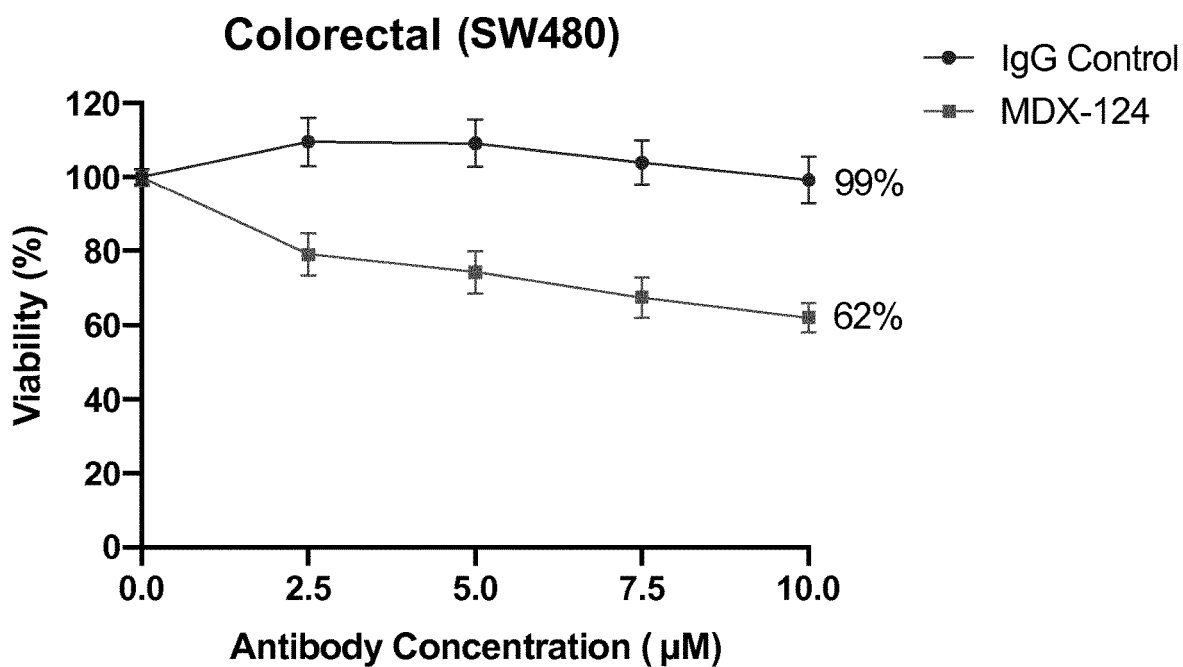

FIG. 14 shows the effect of the anti-Anx-A1 antibody MDX-124 and a non-specific control IgG on the proliferation of the colorectal cancer cell line SW480. Error bars indicate standard error of the mean.

Figure 15:
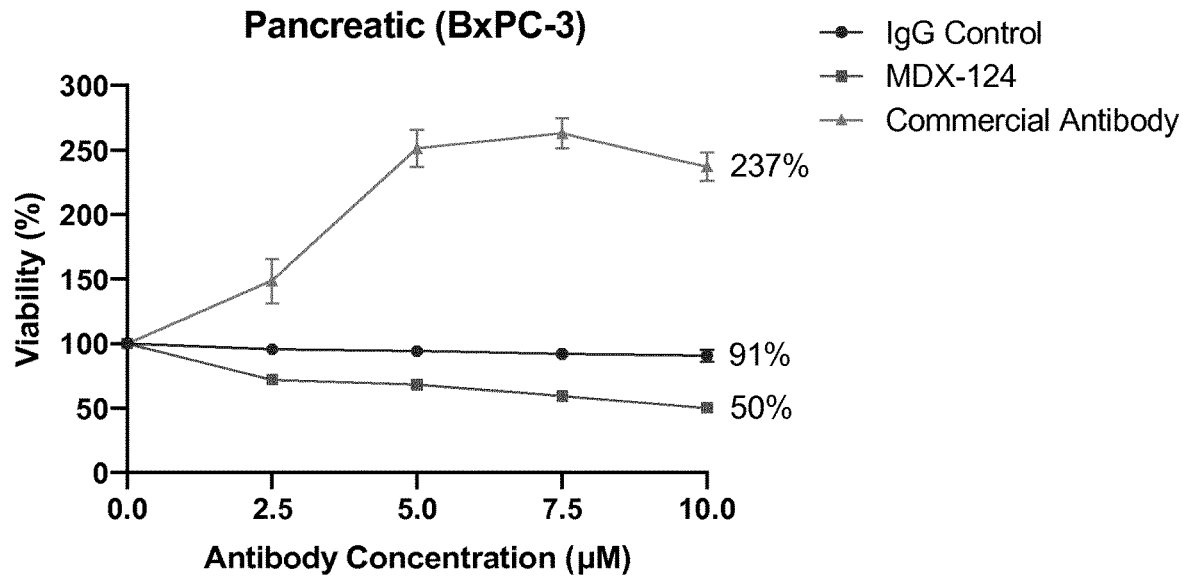

FIG. 15 shows the effect of the anti-Anx-A1 antibodies MDX-124 and ab65844 on the proliferation of the pancreatic cancer cell line BxPC-3. The impact of a non-specific control IgG is also shown. Error bars indicate standard error of the mean.

Figure 16:
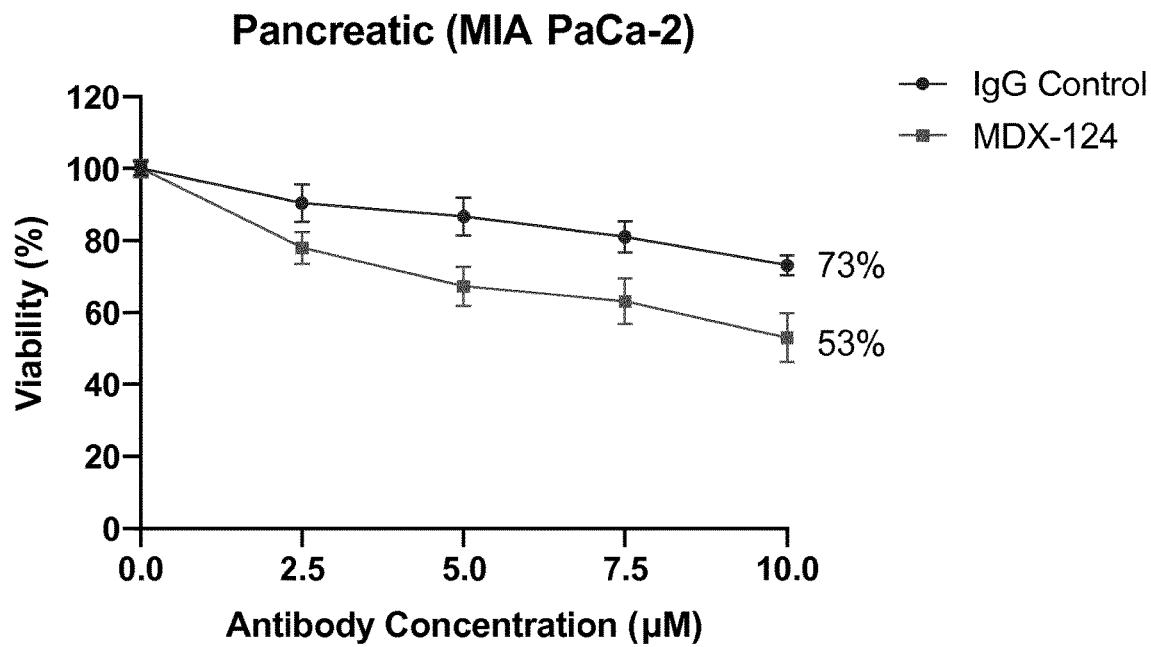

FIG. 16 shows the effect of the anti-Anx-A1 antibody MDX-124 and a non-specific control IgG on the proliferation of the pancreatic cancer cell line MIA PaCa-2. Error bars indicate standard error of the mean.

Figure 17:
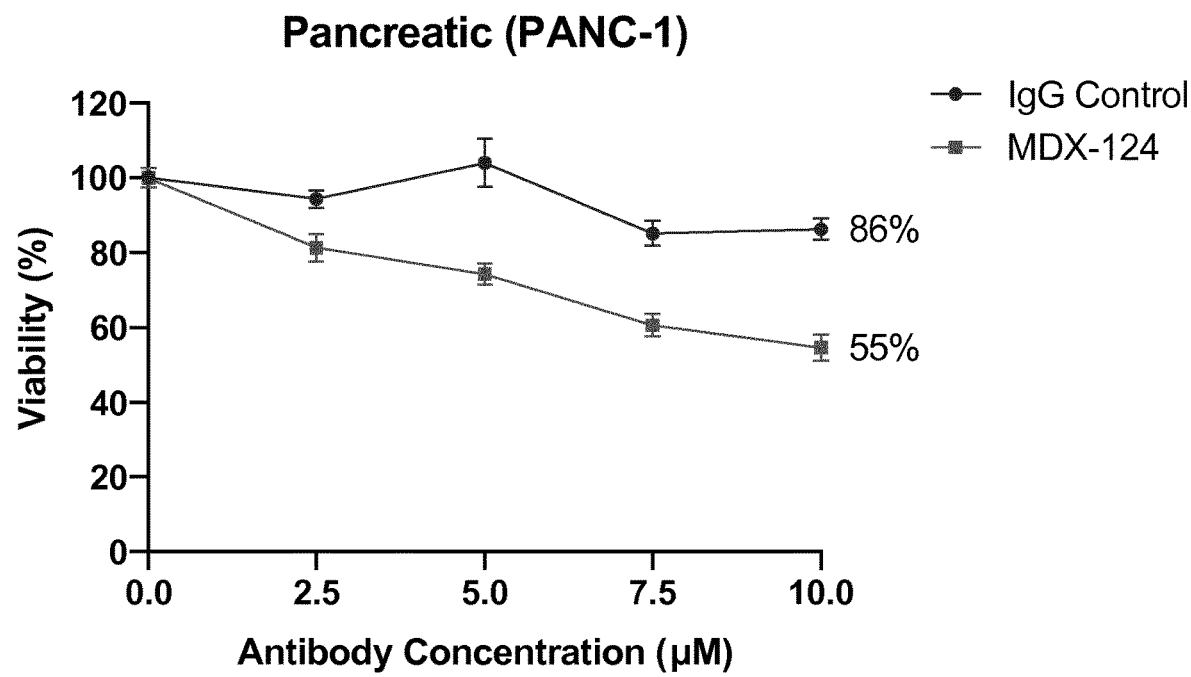

FIG. 17 shows the effect of the anti-Anx-A1 antibody MDX-124 and a non-specific control IgG on the proliferation of the pancreatic cancer cell line PANC-1. Error bars indicate standard error of the mean.

Figure 18:
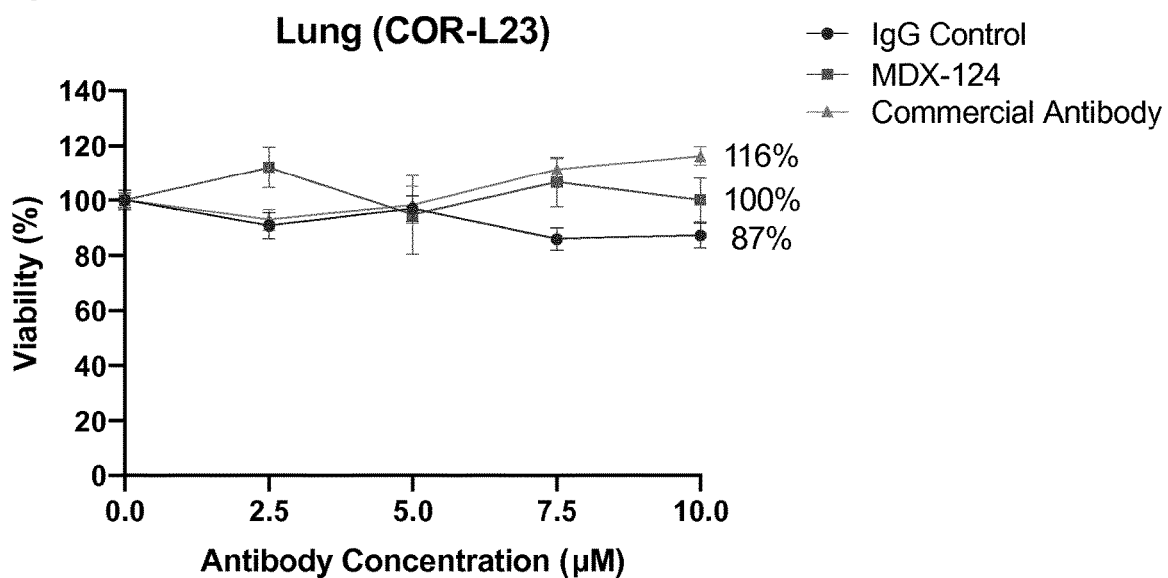

FIG. 18 shows the effect of the anti-Anx-A1 antibodies MDX-124 and ab65844 on the proliferation of the lung cancer cell line COR-L23. The impact of a non-specific control IgG is also shown. Error bars indicate standard error of the mean.

Figure 19:
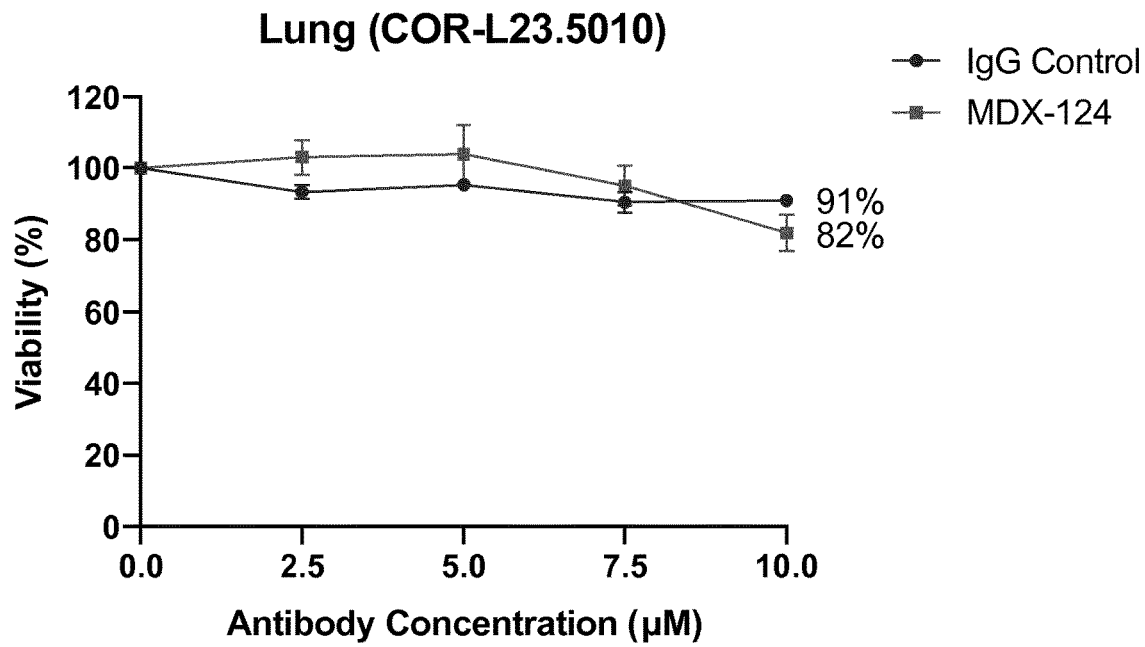

FIG. 19 shows the effect of the anti-Anx-A1 antibody MDX-124 and a non-specific control IgG on the proliferation of the adriamycin-resistant lung cancer cell line COR-L23.5010. Error bars indicate standard error of the mean.

Figure 20:
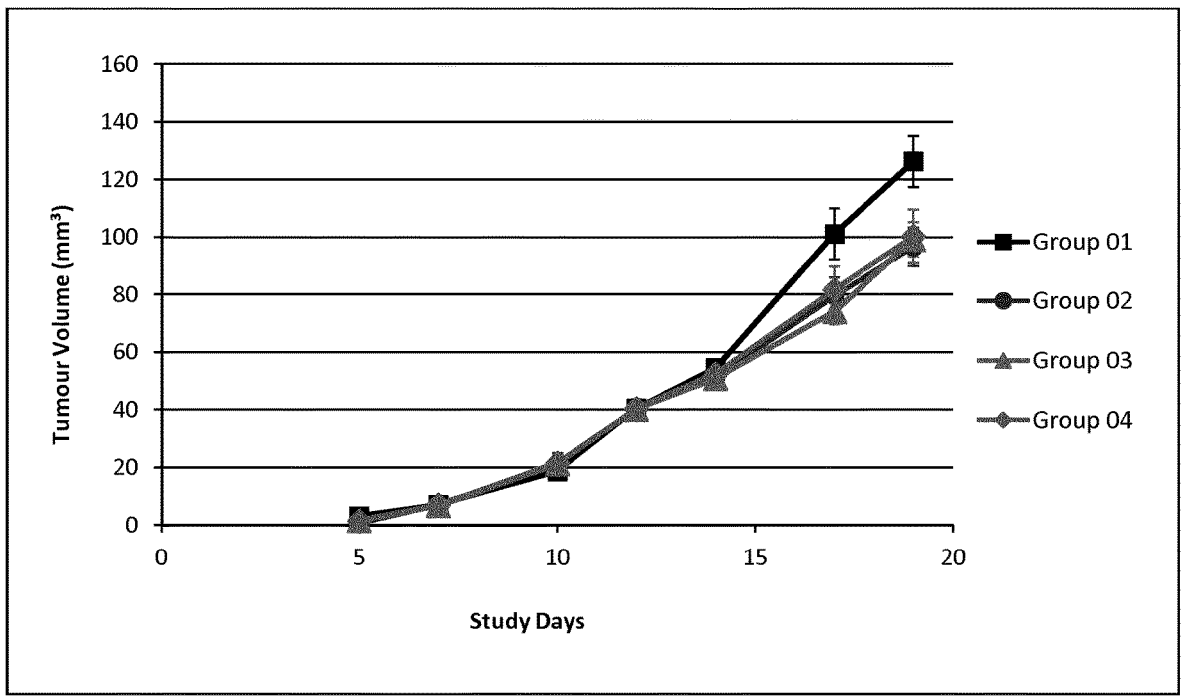

FIG. 20 shows the results of MDX-124 treatment in a mouse model of breast cancer. The figure shows average tumour volumes for the four treatment groups. Group 1 is the control group, administered doses of vehicle only (PBS). Group 2 was administered doses of 1 mg/kg MDX-124, Group 3 was administered doses of 10 mg/kg MDX-124, Group 4 was administered doses of 25 mg/kg MDX-124. Error bars indicate standard error of the mean.

Figure 21:
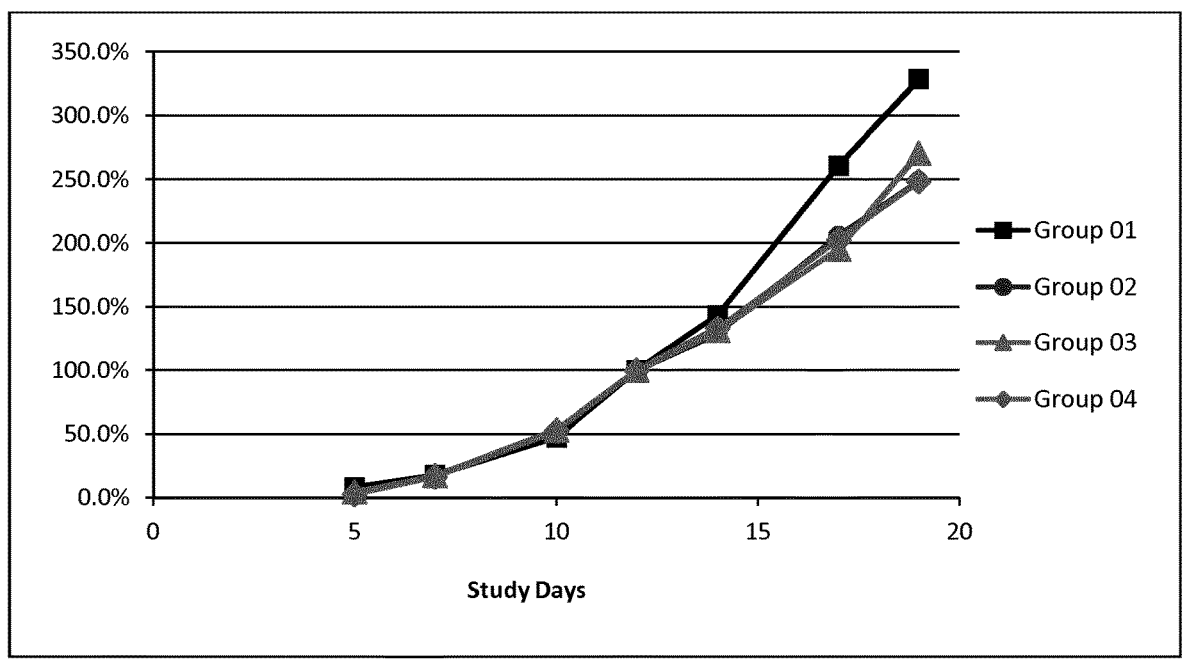

FIG. 21 shows the results of MDX-124 treatment in a mouse model of breast cancer. The figure shows mean relative tumour volumes for the four treatment groups. Group 1 is the control group, administered doses of vehicle only (PBS). Group 2 was administered doses of 1 mg/kg MDX-124, Group 3 was administered doses of 10 mg/kg MDX-124, Group 4 was administered doses of 25 mg/kg MDX-124. The tumour volume on day 12, the day of the first treatment dose, is defined as the baseline tumour volume, i.e. a relative tumour volume of 100%. The relative tumour volumes presented thus correspond to the volume of each tumour as a percentage of its volume at day 12.

EXAMPLES

Example 1—Effect of Antibodies on Cell Proliferation

Materials

The cell lines MCF7, MCF-7/TAMR7, A2780, A2780cis, A2780ADR, HCT116, Caco-2, SW480, COR-L23, COR-L23.5010, MIA-PaCa-2, PANC-1 and BxPC-3 were obtained from Public Health England Culture Collections. The HCC1806 cell line was obtained from the ATCC. MCF7 is a human breast adenocarcinoma cell line positive for the oestrogen receptor and progesterone receptor; MCF-7/TAMR7 is a tamoxifen-resistant derivative of MCF7; HCC1806 is a triple-negative human breast cancer cell line; A2780 is a human ovarian carcinoma cell line; A2780cis is a cisplatin-resistant human ovarian carcinoma cell line (derived from A2780); A2780ADR is an adriamycin-resistant human ovarian carcinoma cell line (derived from A2780); MIA PaCa-2 is a human pancreatic carcinoma cell line; BxPC-3 is a human pancreatic adenocarcinoma cell line; PANC-1 is a human pancreatic epithelioid carcinoma cell line; Caco-2 is a human colorectal adenocarcinoma cell line; HCT116 is a human colorectal carcinoma cell line; SW480 is a human colorectal adenocarcinoma cell line; COR-L23 is a human lung large cell carcinoma cell line; COR-L23.5010 is an adriamycin-resistant derivative of COR-L23.

The L1M2H4 and L2M2H2 anti-Anx-A1 antibodies are disclosed in WO 2018/146230 with sequences as described herein. The L1M2H4 antibody has a light chain with the amino acid sequence set forth in SEQ ID NO: 13 and a heavy chain with the amino acid sequence set forth in SEQ ID NO: 14; the L2M2H2 antibody has a light chain with the amino acid sequence set forth in SEQ ID NO: 15 and a heavy chain with the amino acid sequence set forth in SEQ ID NO: 16.

The anti-Anx-A1 antibody ab65844 was obtained from Abcam (UK). The antibody is a polyclonal rabbit antibody that binds human Anx-A1 amino acids 3-24 (SEQ ID NO: 30). This epitope sequence forms part of the N-terminal region of Anx-A1 which, in the absence of $Ca^{2+}$ binds within a pocket in the Anx-A1 core, discussed above.

Methods

Cell Culture

In the initial proliferation assays cells were cultured in the following media: DMEM+ Glutamax, 10% FBS+pen/strep (MCF7, MIA PaCa-2, HCC1806), RPMI 1640+2 mM L-glu, 10% FBS+pen/strep (BxPc-3, A2780). A2780cis and A2780ADR were cultured in same growth media as A2780 but included the respective drug at various stages of culture to maintain drug resistance (i.e. cisplatin for A2780cis and adriamycin for A2780ADR).

In the further proliferation assays, cells were cultured in the following media under the following conditions:
MCF7, HCC1806, MIA PaCa-2 and PANC-1 in DMEM containing 10% FBS, 1% pen/strep and 1% L-glutamine;
MCF7/TAMR7 in phenol red-free DMEM/F12 containing 1% FBS, 1% pen/strep, 1% L-glutamine and 1% insulin;
A2780, COR-L23, COR-L23.5010 and BxPC-3 in RPMI containing 10% FBS, 1% pen/strep and 1% L-glutamine;
HCT116 in McCoy's 5A containing 10% FBS, 1% pen/strep and 1% L-glutamine;
SW480 in L-15 containing 10% FBS, 1% pen/strep and 1% L-glutamine;
Caco-2 in MEM containing 10% FBS, 1% pen/strep, 1% L-glutamine and 1% non-essential amino acid solution.

Additionally, COR-L23.5010 was cultured in the presence of adriamycin, to maintain drug resistance. All cell lines were cultured at 37° C. in an atmosphere containing 5% $CO_2$.

Cell Proliferation Assay

Cell proliferation was measured using the MTT colorimetric assay to measure cell metabolic activity. In the assay, NADPH-dependent cellular oxidoreductase enzymes reduce the yellow tetrazolium dye, MTT, to an insoluble purple formazan product, quantified by measuring absorbance at 500-600 nm using a spectrophotometer. The quantity of the formazan is proportional to the level of cell proliferation with rapidly dividing cells reducing a higher level of MTT. Assays were performed in triplicate. Cells were seeded in a final volume of 100 µL.

In the initial proliferation assays cells were seeded at the following densities: $1 \times 10^5$/mL (MCF7, MIA PaCa-2 and n=2 of A2780cis), $2 \times 10^5$/mL (A2780, A2780ADR and n=1 of A2780cis), $5 \times 10^4$/mL (HCC1806) and $2.5 \times 10^4$/mL (BxPC-3).

In the further proliferation assays cells were seeded at the following densities:
MCF7, HCC1806, A2780, A2780ADR, A2780cis, COR-L23 and HCT116 at $5 \times 10^3$ cells per well;
MCF7/TAMR7, COR-L23.5010, SW480, Caco-2, MIA PaCa-2, BxPC-3 and PANC-1 at $1 \times 10^4$ per well.

Cells were then cultured for 24 hr prior to assay, then cell proliferation was measured. Cell proliferation was measured following one of the following protocols:
(a) 48 hr culture in the absence of antibody (as control), with 1 µM antibody (either L1M2H4 or L2M2H2) or 10 µM antibody (either L1M2H4 or L2M2H2). MTT assays were performed on the various cancer cell lines on up to three separate occasions (initial proliferation assays); or
(b) 72 hr culture in the absence of antibody, or in the presence of antibody at a concentration of 2.5, 5, 7.5 or 10 µM. The antibodies used in this protocol were L1M2H4 (also referred to herein as MDX-124), the commercially-available anti-Anx-A1 antibody ab65844, and a non-Anx-A1-specific IgG as isotype control (Thermo Fisher Scientific, USA, catalogue number 31154) (further proliferation assays).

Cell number of the control culture was defined as the baseline count for the proliferation assay. Cell counts for cultures in which an antibody was present were normalised to the baseline, and presented as a percentage of the baseline value (referred to as "viability"). Statistical analysis of cell proliferation assay results was performed using the Mann-Whitney U test.

ELISA

ELISA was performed by The Antibody Company (UK) using standard ELISA techniques. ELISA plates were coated with 25 µg/ml full-length Anx-A1 or Anx-A1 N-terminal peptide (corresponding to Anx-A1 amino acids 2-26, SEQ ID NO: 31) and coating buffer (45 mM $Na_2CO_3$, pH 9.6 supplemented with 1 mM $CaCl_2$) for 17 hr at 4° C. Plates were then blocked for 1.5 hr at room temperature with blocking buffer (1 mM $CaCl_2$, 10 mM HEPES, 2% w/v BSA).

Primary antibody (ab65844) was then applied to the plates. The antibody was applied in duplicate in four-fold dilutions made across the plate, starting at a concentration of 1 µg/ml and ending at a concentration of $2.38 \times 10^7$ µg/ml. The antibody was diluted in wash buffer (10 mM HEPES, 150 mM NaCl, 0.05% (v/v) TWEEN-20 and 1 mM $CaCl_2$) supplemented with 0.1 BSA. The primary antibody was applied to the plate for 1 hr at room temperature, and the plate then washed with wash buffer.

The detection antibody was then applied. For detection a horseradish peroxidase (HRP)-conjugated goat anti-rabbit antibody was used (Merck KGaA, Germany; catalogue number AP156P) at a dilution of 1:3000. This was applied to the ELISA plate for 1 hour at room temperature. The ELISA plate was then washed again with wash buffer.

The colorimetric substrate OPD (o-phenylenediamine dihydrochloride, Sigma-Aldrich P4664) was then applied to the plate. OPD solution was made up according to the manufacturer's instructions to yield a 0.4 mg/ml OPD solution in phosphate-citrate buffer, pH 5. 40 µl of 30% $H_2O_2$ was added per 100 ml OPD solution immediately prior to use. 100 µl of the resultant OPD solution was then added to each well of the plate.

The plate was incubated for 20 mins in the dark at room temperature, after which 50 µl of 3 M $H_2SO_4$ was added to stop the reaction. Immediately after addition of $H_2SO_4$ the absorbances of the plate were read at 492 nm.

Results

The commercially-acquired anti-Anx-A1 antibody_ab65844 was tested by ELISA to confirm binding to its reported epitope. The assay demonstrated that antibody ab65844 binds both to full-length Anx-A1 and an N-terminal Anx-A1 peptide (data not shown), indicating that the reported epitope of amino acids 3-24 of human Anx-A1 (SEQ ID NO: 30) is correct.

Initial Proliferation Assays

The first proliferation assays carried out measured proliferation over 48 hours, and compared the effect of the two antibodies L1M2H4 and L2M2H2 on the cell lines of interest, relative to incubation without any antibody (i.e. using protocol (a) as described above).

Figure 1:
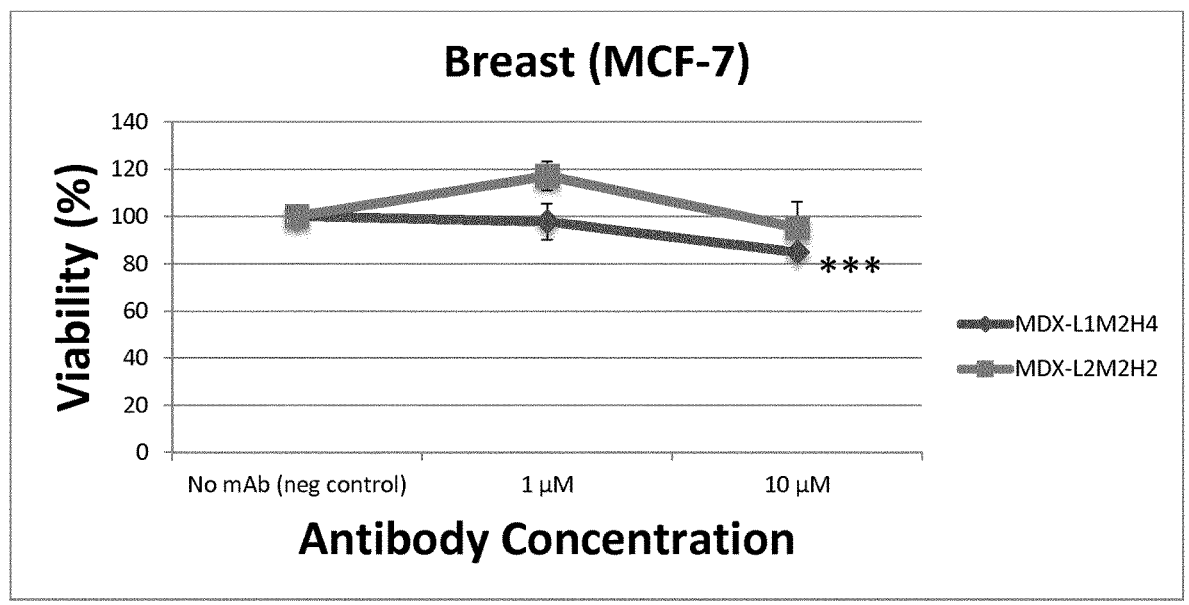
FIG. 1 shows the effect of the anti-Anx-A1 antibodies L1M2H4 and L2M2H2 on the proliferation of the breast cancer cell line MCF7. Error bars indicate standard error of the mean.
Figure 2:
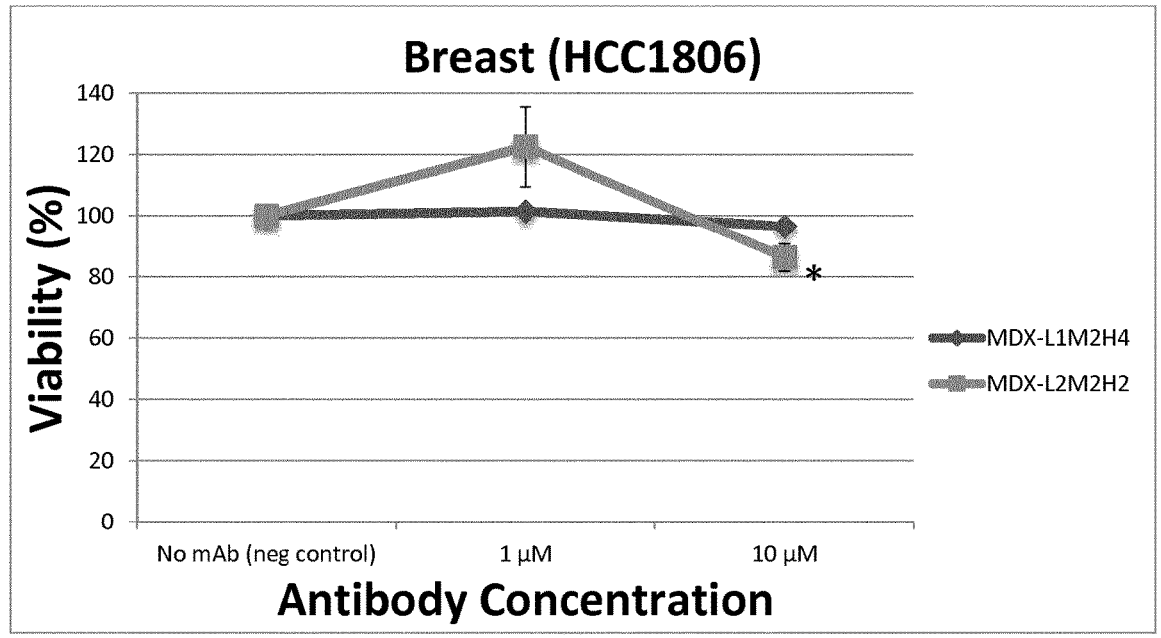
FIG. 2 shows the effect of the anti-Anx-A1 antibodies L1M2H4 and L2M2H2 on the proliferation of the breast cancer cell line HCC1806. Error bars indicate standard error of the mean.

The results of these proliferation assays with the breast cancer cell lines are shown in FIGS. 1 & 2. As shown, the L1M2H4 antibody had a statistically significant effect (p<0.001) at 10 µM, reducing proliferation of the MCF7 cells although this was only n=1. In the HCC1806 cell line, the L2M2H2 antibody also showed a statistically significant decrease in proliferation (p<0.05) at 10 µM (n=2).

Figure 3:
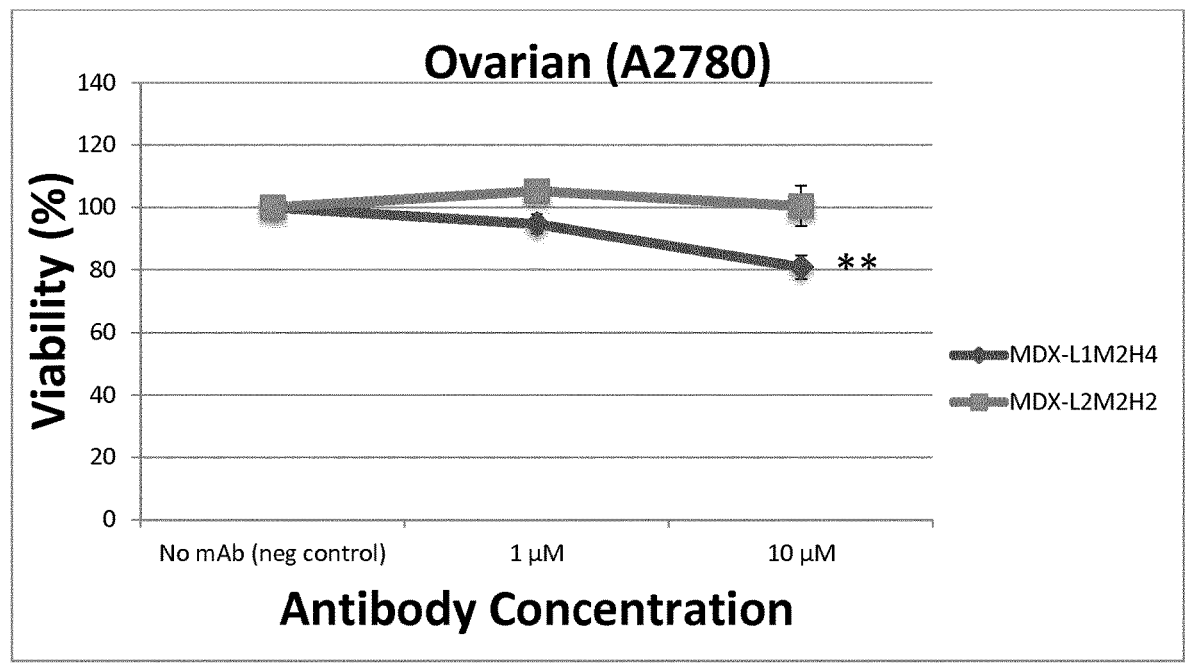
FIG. 3 shows the effect of the anti-Anx-A1 antibodies L1M2H4 and L2M2H2 on the proliferation of the ovarian cancer cell line A2780. Error bars indicate standard error of the mean.
Figure 4:
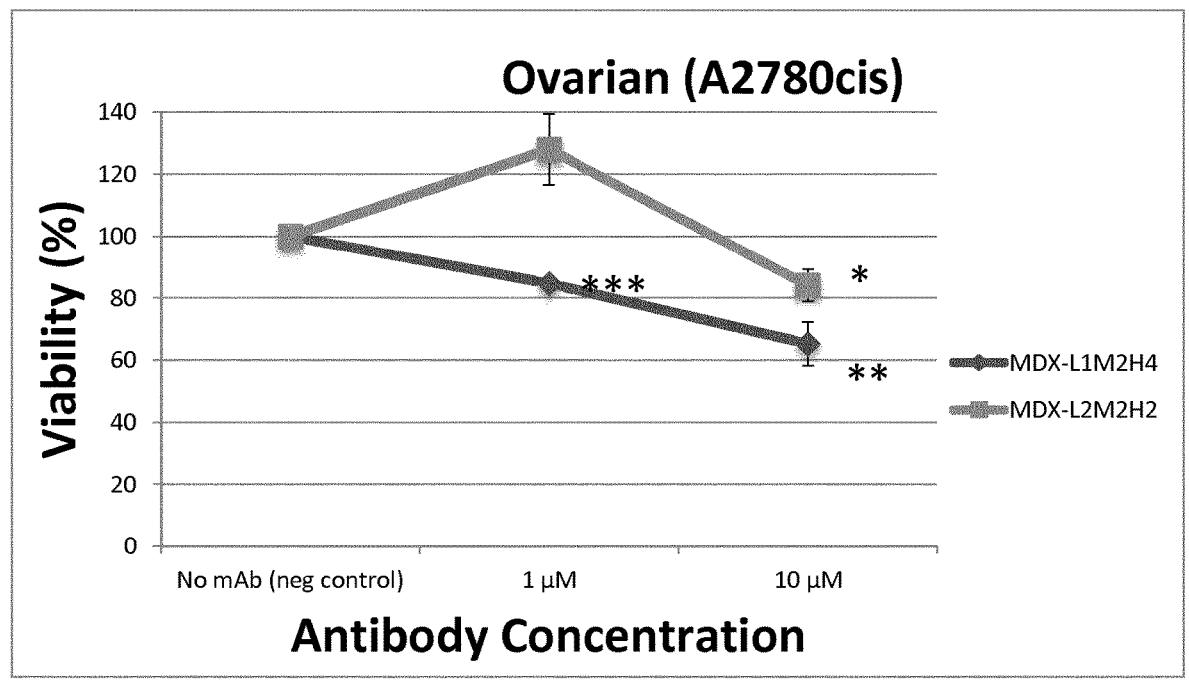
FIG. 4 shows the effect of the anti-Anx-A1 antibodies L1M2H4 and L2M2H2 on the proliferation of the ovarian cancer cell line A2780cis. Error bars indicate standard error of the mean.
Figure 5:
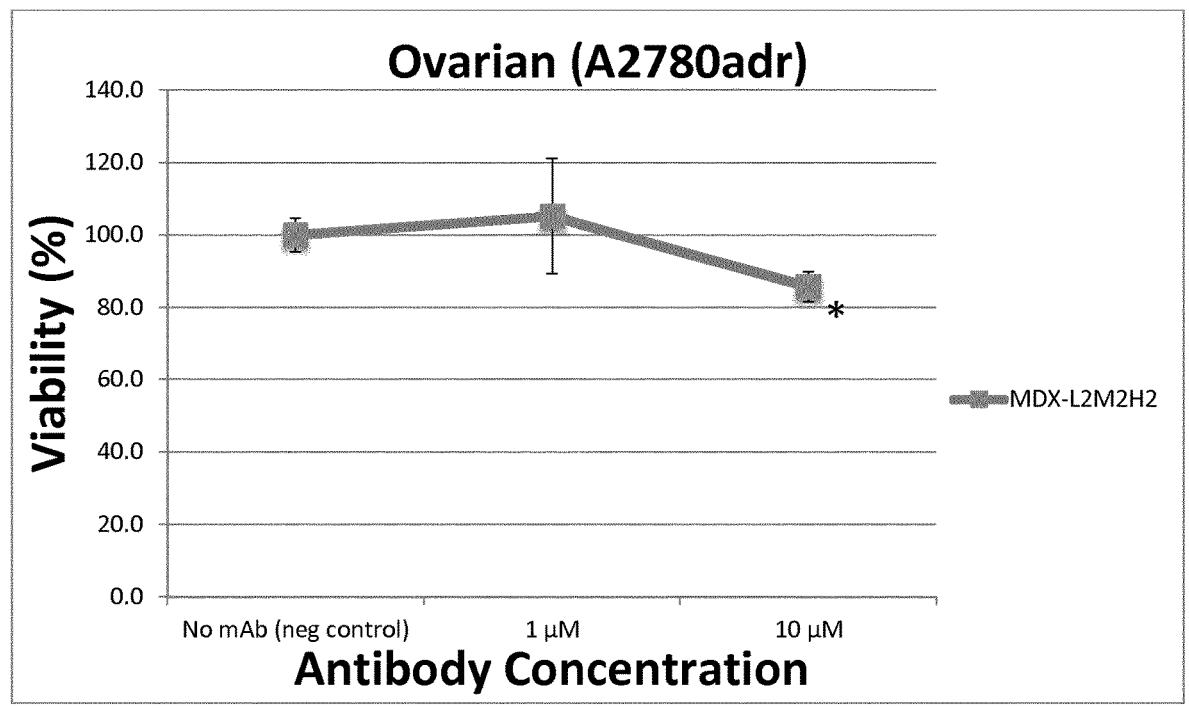
FIG. 5 shows the effect of the anti-Anx-A1 antibody L2M2H2 on the proliferation of the ovarian cancer cell line A2780ADR. Error bars indicate standard error of the mean.

The results of the proliferation assay with the ovarian cancer cell line, A2780, are shown in FIG. 3. As shown, a statistically significant reduction in proliferation was seen following incubation with the L1M2H4 antibody at 10 µM, p<0.01) (n=2). In the cisplatin resistant ovarian cancer cell line, A2780cis (FIG. 4), a statistically significant reduction in proliferation was seen following incubation with the L1M2H4 antibody at 1 µM (p<0.001) and 10 µM (p<0.01) (n=2) with a statistically significant decrease in proliferation observed with the L2M2H2 antibody at 10 µM (p<0.05) (n=3). The results of the proliferation assays with the adriamycin resistant ovarian cancer cell line, A2780ADR are shown in FIG. 5. The L2M2H2 antibody had a significant effect on proliferation of these cells.

Figure 6:
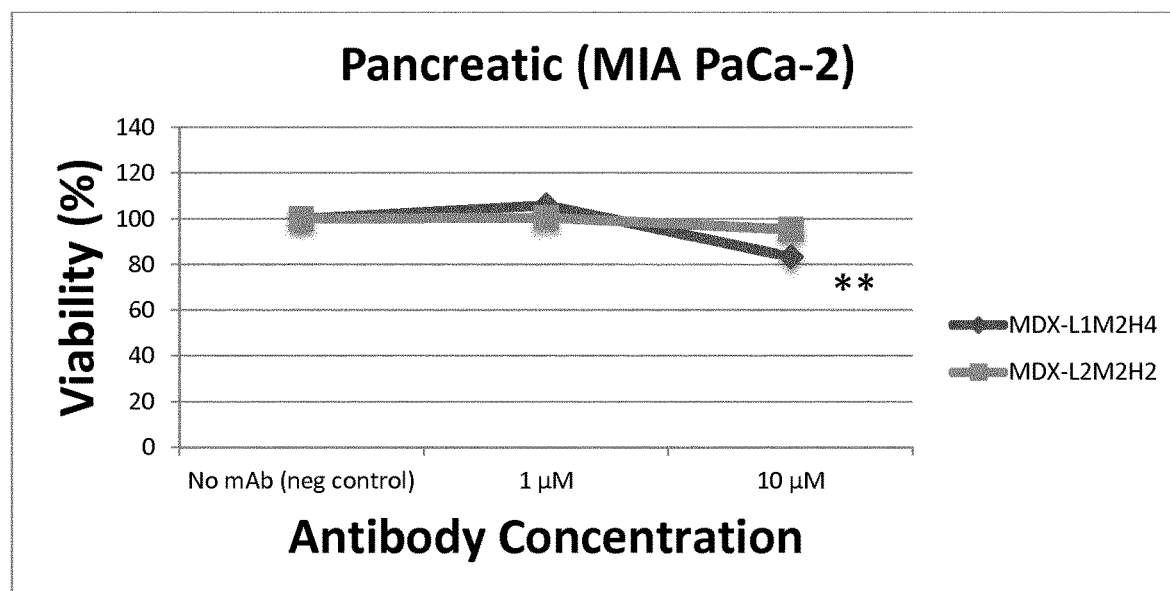
FIG. 6 shows the effect of the anti-Anx-A1 antibodies L1M2H4 and L2M2H2 on the proliferation of the pancreatic cancer cell line MIA PaCa-2. Error bars indicate standard error of the mean.
Figure 7:
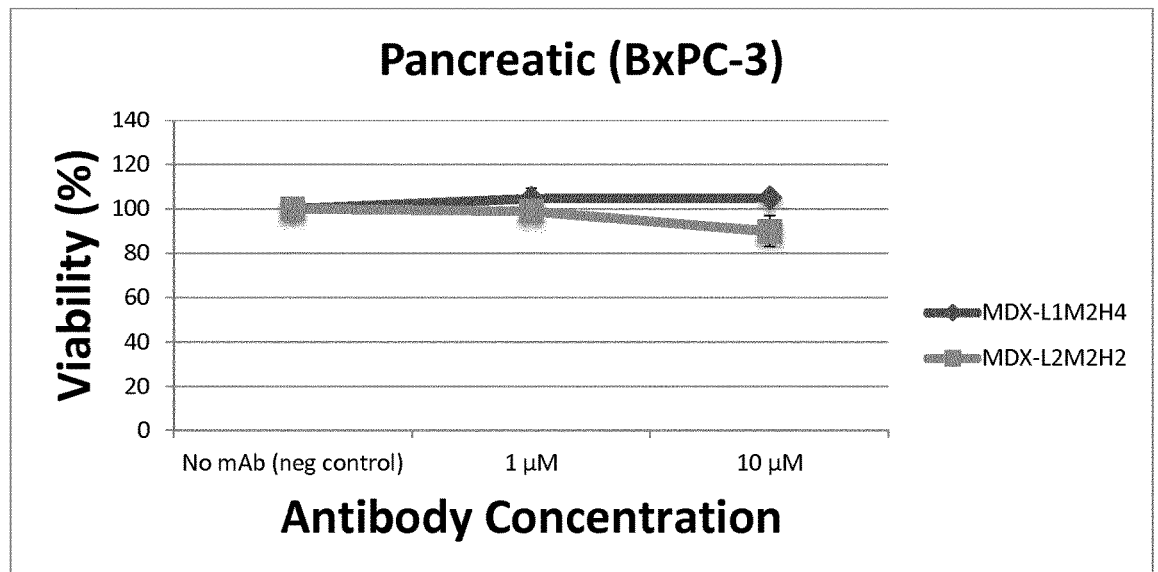
FIG. 7 shows the effect of the anti-Anx-A1 antibodies L1M2H4 and L2M2H2 on the proliferation of the pancreatic cancer cell line BxPC-3. Error bars indicate standard error of the mean.

The results of the proliferation assays with the pancreatic cancer cell lines are shown in FIGS. 6 & 7.

Further Proliferation Assays

The proliferation assays were repeated, measuring proliferation over 72 hours. These assays compared the effect of one antibody of the invention (L1M2H4, also known as MDX-124) with the effect on proliferation of a non-specific IgG control and, where indicated, the commercially-available anti-Anx-A1 antibody ab65844. Comparison to proliferation in the absence of any antibody was also performed and used as the baseline. All experiments were performed in triplicate (for MDX-124 and the IgG control, and where ab65844 was also tested, experiments using this antibody were performed in duplicate).

MDX-124 was found to have a significant effect on proliferation of the HCC1806 breast cancer cell line, causing an almost two-thirds reduction (63%) in viability relative to the baseline (FIG. 8). The non-specific IgG control had no effect on viability. Relative to the non-specific IgG control, MDX-124 was found to cause a statistically significant reduction in HCC1806 cell viability at all tested concentrations, with a P value of <0.001 (at an antibody concentration of 2.5 µM) or <0.0001 (at all other antibody concentrations). Notably, the polyclonal anti-Anx-A1 antibody ab65844 actually caused an increase in cell viability (and thus proliferation). Indeed, at all antibody concentrations MDX-124 was found to cause a statistically significant reduction in HCC1806 cell viability relative to ab65844, with a P value of <0.01 (at an antibody concentration of 2.5 µM) or <0.001 (at all other antibody concentrations). This result demonstrates that MDX-124 inhibits the proliferation of HCC1806 cells (causing a significant reduction in viability). This effect is not, however, seen for all anti-Anx-A1 antibodies, in that ab65844 has the opposite effect on cell viability.

MDX-124 was also found to have significant effects on proliferation of the breast cancer cell line MCF7, and its tamoxifen-resistant derivative (FIGS. 9 & 10, respectively). In both instances, the non-specific IgG control reduces proliferation by up to 26%. At its maximum concentration MDX-124 causes a significant 76% reduction in viability of MCF7 cells, and also a significant (though lower) 47% reduction in the viability of tamoxifen-resistant MCF7 cells. Relative to the non-specific IgG control, MDX-124 was found to cause a statistically significant reduction in MCF7 cell viability at all tested concentrations with a P value of <0.0001. MDX-124 was also found to cause statistically significant reductions in MCD7/TAMR7 cell viability, relative to the non-specific IgG control, at concentrations of 5 and 7.5 µM (P<0.01) and 10 µM (P<0.05). These results show that MDX-124 is highly effective in inhibiting the proliferation of breast cancer cells, of both triple-negative and hormone receptor positive cell lines. The antibody is also effective against drug-resistant breast cancer. This effect is specific to MDX-124, and is not seen in all anti-Anx-A1 antibodies.

Similarly, MDX-124 was found to have a significant effect on proliferation of the ovarian cancer cell line A2780 (FIG. 11). While the non-specific IgG reduces proliferation by up to 30% (at the maximum concentration), MDX-124 has more than double the effect on proliferation (causing a 61% reduction in proliferation at the maximum concentration). Relative to the non-specific IgG control, MDX-124 was found to cause a statistically significant reduction in A2780 cell viability at concentrations of 5 and 7.5 µM ($P<0.05$) and 10 µM ($P<0.01$). Again, this is not seen for the polyclonal anti-Anx-A1 antibody ab65844, which caused no significant impact on proliferation. For this antibody, slightly increased proliferation was seen at low concentrations of this antibody (up to 5 µM), while at the maximum concentration a modest reduction in proliferation of 5% was seen. Indeed, at antibody concentrations of 5, 7.5 and 10 µM MDX-124 was found to cause a statistically significant reduction in A2780 cell viability relative to ab65844, with a P value of <0.001.

MDX-124 was also found to have a substantial impact on proliferation of colorectal cancer cells (FIGS. 12-14). The results on the proliferation of the HCT116 cell line are shown in FIG. 12. MDX-124 more than halves proliferation of these cells (reducing proliferation by up to 54% at the maximum concentration). The non-specific IgG control has no real impact on proliferation, and the polyclonal anti-Anx-A1 antibody ab65844 had varying impacts at the different concentrations. Relative to the non-specific IgG control, MDX-124 was found to cause a statistically significant reduction in HCT116 cell viability at all tested concentrations with a P value of <0.001 (at antibody concentrations of 2.5 and 7.5 µM) or <0.0001 (at antibody concentrations of 5 and 10 µM). While the data for ab65844 is slightly inconsistent, there is a clear general trend of the antibody again driving increased proliferation of the cancer cells, and relative to ab65844, MDX-124 was found to cause statistically significant reductions in HCT116 cell viability at antibody concentrations of 2.5 µM ($P<0.01$) and 5 and 10 µM (both $P<0.001$). No data point suggests that ab65844 causes a reduction in proliferation.

The results using the cell lines Caco-2 (FIG. 13) and SW480 (FIG. 14) tell a similar story, in that MDX-124 causes a significant reduction in proliferation, while the non-specific IgG control has at most minimal impact. Relative to the non-specific IgG control, MDX-124 was found to cause a statistically significant reduction in Caco-2 cell viability at all tested concentrations, with a P value of <0.05 (at antibody concentrations of 2.5 and 5 µM) or <0.001 (at antibody concentrations of 7.5 and 10 µM). Relative to the non-specific IgG control, MDX-124 was found to cause a statistically significant reduction in SW480 cell viability at all tested concentrations, with a P value of <0.01 (at an antibody concentration of 2.5 µM) or <0.0001 (at all other tested antibody concentrations). These results demonstrate that MDX-124 is highly effective in inhibiting the proliferation of colorectal cancer cells. Again, this effect is specific to MDX-124, not being seen in all anti-Anx-A1 antibodies.

The impact of MDX-124 on pancreatic cancer cell lines is shown in FIGS. 15-17. The impact of MDX-124 on the cell line BxPC-3 is shown in FIG. 15. Again, MDX-124 has a significant impact on cell proliferation, reducing proliferation by half at the maximum concentration. The non-specific IgG control had minimal impact on proliferation, while again the polyclonal anti-Anx-A1 antibody ab65844 drove a significant increase in proliferation. Relative to the non-specific IgG control, MDX-124 was found to cause a statistically significant reduction in BxPC-3 cell viability at all tested concentrations, with a P value of <0.001 (at an antibody concentration of 2.5 µM) or <0.0001 (at all other tested antibody concentrations). Relative to ab65844, MDX-124 was found to cause a statistically significant reduction in BxPC-3 cell viability with a P value of <0.001 at all tested antibody concentrations.

The impact of MDX-124 on the cell lines MIA PaCa-2 and PANC-1 is shown in FIGS. 16 and 17, respectively. In both instances, MDX-124 causes a significant reduction in proliferation of almost half, while the non-specific IgG causes much lesser reductions in viability. Relative to the non-specific IgG control, MDX-124 was found to cause a statistically significant reduction in MIA PaCa-2 cell viability at antibody concentrations of 5 and 10 µM, with a P value of <0.05. Relative to the non-specific IgG control, MDX-124 was found to cause a statistically significant reduction in PANC-1 cell viability at all antibody concentrations, with a P value of <0.05 (at an antibody concentration of 2.5 µM) or <0.001 (at all other tested antibody concentrations).

The impact of MDX-124 on the lung cancer cell lines COR-L23 and COR-L23.5010 is shown in FIGS. 18 & 19, respectively. These results show that the MDX-124 antibody has a modest but negative effect on proliferation, whereas the non-specific IgG control and the polyclonal anti-Anx-A1 antibody ab65844 showed very little effect on proliferation. Similar results were obtained with other lung cancer cell lines (data not shown).

Conclusions

Exposure to MDX-124 causes a significant reduction in proliferation of cell lines from breast cancer (including triple negative, hormone receptor positive and drug-resistant cell lines), colorectal cancer, ovarian cancer, lung cancer and pancreatic cancer.

The impact of MDX-124 on cancer cell proliferation is antibody-specific, i.e. not all antibodies against the same target (Anx-A1) have the same impact. This is demonstrated by the fact that the ab65844 failed to significantly reduce proliferation of any of the cell lines it was tested against, and indeed increased proliferation in the majority of cases. The non-specific IgG control also did not cause the significant reduction in proliferation seen using MDX-124.

Example 2—Epitope Determination

HDX analysis was performed at the Natural and Medical Sciences Institute (NMI), University of Tübingen, Germany, using the L1M2H4 antibody.

Sample Preparation and Analysis

Antibody-Antigen Complex Formation and Hydrogen-Deuterium Exchange

Five aliquots of antibody-antigen samples and five aliquots of antigen without antibody were prepared as follows: 0.8 µL Anx-A1 (41 µM), 1.8 µL antibody (38.7 µM) or HEPES buffer (10 mM HEPES, 1 mM $CaCl_2$, 150 mM NaCl pH 7.4) respectively, 1 µL HEPES buffer and 0.5 µL $CaCl_2$ (8 mM) were mixed and incubated for 10 minutes at 20° C. 8.5 µL HEPES buffer was added to adjust the salt content. The antibody-antigen complex was lyophilized over night at 0° C. and subsequently at 15° C. for 2 h to remove as much water as possible. The ten lyophilized aliquots were frozen at −20° C. until HDX-exchange and LC-MS analysis. One aliquot of each of the antibody-antigen complex and the antigen without antibody was solubilized in 12.5 µl $H_2O$, the others in 12.5 µL $D_2O$. Aliquots were incubated for the following times, whereby each aliquot was prepared separately right before analysis:

0 minutes ($H_2O$ reference samples);
5, 70, 360 minutes and 24 hours ($D_2O$ deuterium exchange kinetic samples).

The exchange was quenched by addition of 12.5 µL of freshly prepared quenching solution (guanidine hydrochloride 0.8 M with TCEP 0.4 M in 100 mM ammonium formate buffer pH 2.5).

Peptic Digest

Immediately after addition of the quenching solution, 0.35 µL pepsin (100 µM) were added and digestion performed for 2 minutes at 20° C. Aliquots were placed immediately in −20° C. pre-cooled autosampler vials and injected via a pre-cooled injection syringe into the LC-MS.

LC-MS

The peptide mixture obtained was injected and separated without pretreatment using reverse phase HPLC (RSLC3000 LC, Thermo Scientific Dionex, Idstein, Germany). An LC column (ACQUITY UPLC BEH300 C18 1.7 µm 1×50 mm Thermo Scientific Dionex, Idstein, Germany) was used for separation of the sample. Blank runs and column wash runs were performed within consecutive sample runs.

Chromatographic separation was achieved by using a nearly isocratic gradient for 31 minutes. Eluent A was water with 0.1% formic acid and eluent B was acetonitrile with 0.1% formic acid. An optimized 20-minute linear gradient with varying slopes was applied at −0° C. as follows (minute/% B): 0/8, 3/8, 11.9/20, 31.9/20, 33/99, 34/99, 35/8. Manual injection was performed. The injection amount was 25.35 µL using a sample loop of 20 µL volume. Flow rate was 40 µL/min. The HPLC eluate was directly infused into a QTOF-type mass spectrometer (MaXis HD, Bruker). The mass spectrometer operated in positive ion mode, the spray voltage was 1.9 kV, the capillary temperature was 275° C. and the S-Lens RF voltage was 55 V.

Data Analysis

The data was analysed using the software HDExaminer 2.40 beta 1 64 bit (Sierra Analytics, Modest, CA, USA). Briefly, a raw dataset containing different exchange time points, and for each time point the analysis of Anx-A1 with and without antibody was examined. Using the Anx-A1 sequence information and a sequence list of peptic peptides with corresponding retention times and charge, the software identifies the peptides with and without deuterium exchange and calculates the deuterium uptake per peptide as being the difference between the centroid mass of the deuterated versus the non-deuterated peptide. By using overlapping peptide information (mass shift of individual overlapping peptides) the epitope region was manually further limited.

Results

After the initial data evaluation using HDExaminer the individual peptic peptides were manually verified for a statistically relevant uptake of deuterium. In case of several overlapping peptides, the epitope region was further limited using HDX-data without deuterium uptake covering the N- and C-terminal parts of the peptide with deuterium uptake. The whole experiment was repeated twice. In the first experiment identified a potential epitope region was identified but a statistically relevant deuterium uptake was also observed in a very long peptide containing the N-terminus, which from a structural point of view is rather flexible. In the second experiment it was possible to confirm the epitope region, while the N-terminus showed no deuterium uptake.

The underlined regions in the sequence indicate the epitope bound by the antibody:

(SEQ ID NO: 17)
MAMVSEFLKQAWFIENEEQEYVQTVKSSKGGPGSAVSPYPTFNPSSDVAA

LHKAIMVKGVDEATIIDILTKRNNAQRQQIKAAYLQETGKPLDETLKKAL

TGHLEEVVLALLKTPAQFDADELRAAMKGLGTDEDTLIEILASRTNKEIR

-continued
DINRVYREELKRDLAKDITSDTSGDFRNALLSLAKGDRSEDFGVNEDLAD

SDARALYEAGERRKGTDVNVFNTILTTRSYPQLRRVFQKYTKYSKHDMNK

VLDLELKGDIEKCLTAIVKCATSKPAFFAEKLHQAMKGVGTRHKALIRIM

VSRSEIDMNDIKAFYQKMYGISLCQAILDETKGDYEKILVALCGGN

The identified epitope regions are not in the Anx-A1 self-interaction region, but peptides from the self-interaction region show a slight tendency to more deuterium uptake in the antibody-antigen complex samples, which might by due to slight differences in local Anx-A1 concentration when two Anx-A1 molecules are bound to the two arms of the antibody.

Example 3—In Vivo Anti-Cancer Activity of MDX-124

Methods

Tolerability Study

The tolerability study was performed by Crown Bioscience (USA). Mice were dosed once per week for 2 weeks with MDX-124 at 1 mg/kg, 10 mg/kg or 29 mg/kg. Body weight of each mouse was measured daily for the duration of the study. A reduction in body weight would be taken as an indication of toxicity of the antibody to the mice.

Murine Breast Cancer Model

Mouse work was performed by Crown Bioscience. The mice used were 8-9 week old female BALB/c mice. The breast cancer model used utilised the luciferase expressing murine breast cancer cell line 4T1-Luc. The cell line was obtained from the ATCC and cultured in RPMI medium containing 10% FBS, 2 mM L-glutamine and 2 µg/ml puromycin.

Mice were shaved, then 72 hours later a transponder chip implanted for the purposes of individual mouse identification. Bepanthen cream was applied immediately following shaving and then daily until tumour inoculation.

Each mouse was first inoculated with $5 \times 10^4$ 4T1-Luc cells, suspended in 100 µl PBS. Inoculation was performed on day 0 into a mammary fat pad (lower left side, $2^{nd}$ pad from bottom) while mice were under gaseous anaesthesia. The skin at the inoculation site was cleaned with 70% ethanol prior to inoculation.

Tumour size was measured three times a week starting from day 5, using an IVIS Spectrum In Vivo Imaging System (PerkinElmer, USA). Bioluminescent imaging was used to measure each tumour in 2 dimensions, using electronic callipers. Tumour volumes were estimated using the formula $0.5(L \times W^2)$, where L=tumour length and W=tumour width. Treatment began when the mean tumour volume reached 50-60 mm³. After the first tumour measurement, bepanthen cream was again applied to the area around the tumour. Bepanthen cream was subsequently applied daily.

The mice were split into 4 groups of 12 mice each, with uniform mean tumour volume between groups. Treatment was administered weekly. Of the four mouse groups, a control group was dosed with vehicle only (PBS). The three experimental groups received doses of 1, 10 or 25 mg/kg MDX-124, in PBS. Each dose was given intravenously in a volume of 10 ml/kg. Treatment was to be continued for up to 3 weeks. Thrice weekly tumour measurement continued following the commencement of treatment. Mice were weighed three times a week prior to treatment commencing, and daily thereafter.

Results

To check that MDX-124 was not inherently toxic to mice a tolerability study was performed. Mice were administered the antibody and their body weights monitored. No body weight loss was evident in the mice (data not shown), indicating that the antibody was not toxic to them at any of the tested doses.

The anti-cancer effect of MDX-124 was then tested in a murine model of breast cancer. Average tumour volumes for each group of mice tested are shown in FIG. 20. Following tumour cell inoculation on day 0, the first treatment dose was administered to all groups on day 12. As shown, by day 17 of the study, mice treated with MDX-124 had significantly lower tumour volumes than the control mice treated with a vehicle. The pattern of increased tumour growth in the control group continued to day 19. The lower tumour volumes seen in the groups treated with MDX-124 also corresponded to lower relative tumour volumes in these groups (see FIG. 21).

The tumour volume at day 12 was defined as the baseline tumour volume (i.e. 100% tumour volume). By day 19 the tumours of the mice treated with MDX-124 had increased in size approximately 2.5-fold. The tumours of the control mice had increased in size approximately 3.3-fold. This means that treatment with MDX-124 resulted in an approximately one-third reduction in tumour growth relative to the control by day 19, demonstrating the anti-cancer effect of the antibody. While the antibody was administered to the mice at three different concentrations (1 mg/kg, 10 mg/kg and 25 mg/kg), each of these treatment regimes had a similar effect on tumour growth (i.e. increasing the amount of antibody administered did not seem to increase the effect of the treatment).

The invention claimed is:

1. A method of treating cancer in a subject, comprising administering to said subject a specific antibody or fragment thereof which binds human Anx-A1 and comprises the complementarity-determining regions (CDRs) VLCDR1, VLCDR2, VLCDR3, VHCDR1, VHCDR2 and VHCDR3, each of said CDRs having an amino acid sequence as follows:
VLCDR1 has the sequence set forth in SEQ ID NO: 1;
VLCDR2 has the sequence set forth in SEQ ID NO: 2;

VLCDR3 has the sequence set forth in SEQ ID NO: 3;
VHCDR1 has the sequence set forth in SEQ ID NO: 4;
VHCDR2 has the sequence set forth in SEQ ID NO: 5; and
VHCDR3 has the sequence set forth in SEQ ID NO: 6.

2. The method of claim 1, wherein said subject is human.

3. The method of claim 1, wherein said antibody or fragment thereof is humanized.

4. The method of claim 1, wherein said antibody is a monoclonal antibody, or said antibody fragment is an Fab, Fab' or F(ab')$_2$ antibody fragment or an scFv molecule.

5. The method of claim 1, wherein said specific antibody or fragment thereof is an antibody or fragment thereof comprising:
   i) a light chain variable region comprising the amino acid sequence set forth in SEQ ID NO: 9 or 10, or an amino acid sequence having at least 70% sequence identity thereto; and
   ii) a heavy chain variable region comprising the amino acid sequence set forth in SEQ ID NO: 11 or 12, or an amino acid sequence having at least 70% sequence identity thereto.

6. The method of claim 5, wherein said specific antibody or fragment thereof is a monoclonal antibody comprising:
   i) a light chain comprising the amino acid sequence set forth in SEQ ID NO: 13, or an amino acid sequence having at least 70% sequence identity thereto; and
   ii) a heavy chain comprising the amino acid sequence set forth in SEQ ID NO: 14, or an amino acid sequence having at least 70% sequence identity thereto.

7. The method of claim 5, wherein said specific antibody or fragment thereof is a monoclonal antibody comprising:
   i) a light chain comprising the amino acid sequence set forth in SEQ ID NO: 15, or an amino acid sequence having at least 70% sequence identity thereto; and
   ii) a heavy chain comprising the amino acid sequence set forth in SEQ ID NO: 16, or an amino acid sequence having at least 70% sequence identity thereto.

8. The method of claim 1, wherein said cancer expresses Anx-A1.

9. The method of claim 8, wherein Anx-A1 is expressed on the surface of cells of said cancer.

10. The method of claim 1, wherein said cancer is resistant to one or more chemotherapeutic agents.

11. The method of claim 10, wherein said cancer is multi-drug resistant.

12. The method of claim 10, wherein said cancer is resistant to platinum-based chemotherapeutic agents.

13. The method of claim 10, wherein said cancer is resistant to cisplatin; adriamycin and/or tamoxifen.

14. The method of claim 1, further comprising the administration of a second therapeutic agent to said subject.

15. The method of claim 14, wherein said second therapeutic agent is a chemotherapeutic agent.

16. The method of claim 15, wherein said chemotherapeutic agent is a cytotoxic agent.

17. The method of claim 1, wherein said cancer is selected from breast cancer, colorectal cancer, ovarian cancer, lung cancer and pancreatic cancer.

* * * * *